US007291325B2

(12) United States Patent
Lee et al.

(10) Patent No.: US 7,291,325 B2
(45) Date of Patent: Nov. 6, 2007

(54) METHOD FOR PRODUCING TARGET PROTEINS BY DELETING OR AMPLIFYING *IBPA* AND/OR *IBPB* GENE CODING FOR INCLUSION BODY-ASSOCIATED PROTEINS

(75) Inventors: Sang Yup Lee, Daejeon (KR); Mee Jung Han, Daejeon (KR); Si Jae Park, Seoul (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 10/545,849

(22) PCT Filed: Jul. 10, 2003

(86) PCT No.: PCT/KR03/01371

§ 371 (c)(1),
(2), (4) Date: Aug. 17, 2005

(87) PCT Pub. No.: WO2004/081202

PCT Pub. Date: Sep. 23, 2004

(65) Prior Publication Data
US 2006/0194277 A1 Aug. 31, 2006

(30) Foreign Application Priority Data
Mar. 14, 2003 (KR) .................... 10-2003-0015965

(51) Int. Cl.
*A61K 48/00* (2006.01)
*A01N 63/00* (2006.01)
*C07H 21/02* (2006.01)
*C07H 21/04* (2006.01)

(52) U.S. Cl. .................. 424/93.2; 424/93.1; 424/184.1; 424/234.1; 424/257.1; 435/41; 435/69.1; 435/71.1; 435/440; 536/23.1; 536/23.7

(58) Field of Classification Search ............... 424/93.1, 424/93.2, 184.1, 234.1, 257.1; 435/41, 69.1, 435/71.1, 440; 536/23.1, 23.7
See application file for complete search history.

(56) References Cited
U.S. PATENT DOCUMENTS
4,758,512 A 7/1988 Goldberg et al.
5,552,301 A 9/1996 Baneyx et al.

OTHER PUBLICATIONS

Thomas, J.G., et al "Roles of the *Excherichia coli* small heat shock proteins IbpA and IbpB in thermal stress management: Comparison with CIpA, CIpB, and HtpG in vivo", Journal of Bacteriology, vol. 180, No. 19, Oct. 1998.*
LaRossa and Van Dyk, *Mol. Microbiol.*, 5, 529-34, 1991.
Goloubinoff, et al., *Nature*, 337, 44-7, 1989.
Georgiou and Valax, *Curr. Opin. Biotechnol.*, 7, 190-7, 1996.
Murby, et al., *Biotechnol. Appl. Biochem.*, 14, 336-46, 1991.
Langer, et al., *Nature*, 356, 683-9, 1992.
Easton, et al., *Gene*, 101, 291-5, 1991.
Obukowicz, et al., *Appl. Environ. Microbiol.*, 58 1511-23, 1992.
Studer and Narberhaus, *J. Biol. Chem.*, 275, 37212-8, 2000.
Allen, et al., *J. Bacteriol.*, 174, 6938-47, 1992.
Nossal, et al., *J. Biol. Chem.*, 241, 3055-62, 1966.
Meerman and Georgiou, *Ann. N.Y. Acad. Sci.*, 721, 292-302, 1994.
Hockney, *TIBTECH*, 12, 456-63, 1994.
Makrides, SC, *Microbiol. Rev.*, 60, 512-38, 1996.
Lee, SY, *Trends Biotechnol.*, 14, 98-105, 1996.
Jeong and Lee, *Appl. Environ. Microbiol.*, 65, 3027-32, 1999.
Kane and Hartley, *Trends Biotechnol.*, 6, 95-101, 1988.
Denefle et al., *Gene*, 56, 61-70, 1987.
Saito, et al., *J. Biochem.*, 101, 1281-88, 1987.
Gill, et al., *Bio/Techol.*, 3, 643-6, 1985.
Weir and Sparks, *Biochem. J.*, 245, 85-91, 1987.
Jeong and Lee, *Appl. Environ. Microbiol.*, 68, 4979-85, 2002.
Brickman and Beckwith, *J. Mol. Biol.*, 96, 307-16, 1975.
Kim and Lee, *J. Biotechnol.*, 48, 97-105, 1996.

* cited by examiner

*Primary Examiner*—Rodney P Swartz
(74) *Attorney, Agent, or Firm*—Steven J. Hultquist; Kelly K. Reynolds; Intellectual Property / Technology Law

(57) ABSTRACT

A method for producing target proteins by deleting or amplifying ibpA and/or ibpB genes coding for inclusion body-associated proteins. Two methods for producing target proteins using ibpA and/or ibpB genes coding for inclusion body-associated proteins of *E. coli* are described. The first method enhances the secretory production and activity of target proteins using ibpA and/or ibpB genes-deleted bacteria. The second method enhances the production of target proteins in the cytoplasm and also converts the target proteins from soluble form to insoluble inclusion body, using ibpA and/or ibpB gene-amplified bacteria.

12 Claims, 20 Drawing Sheets

METHOD FOR PRODUCING TARGET PROTEINS BY DELETING OR AMPLIFYING *IBPA* AND/OR *IBPB* GENE CODING FOR INCLUSION BODY-ASSOCIATED PROTEINS

CROSS-REFERENCE TO RELATED APPLICATIONS

This application is filed under the provisions of 35 U.S.C. §371 and claims the priority of International Patent Application No. PCT/KR2003/001371 filed July 10, 2003, which in turn claims priority of Korean Patent Application No. 10-2003-015965 filed Mar. 14, 2003.

FIELD OF THE INVENTION

The present invention relates to a method for producing target proteins by deleting or amplifying the ibpA and/or ibpB genes coding for inclusion body-associated proteins. More particularly, the present invention relates to a method for the secretory production of target proteins using ibpA and ibpB-deleted bacteria, or producing target proteins in inclusion body form using ibpA and/or ibpB amplified bacteria.

BACKGROUND ART

According to the development of recombinant DNA technology, medically and industrially useful proteins, which could have been obtained at only small amounts in natural conditions, could be produced at large amounts in bacteria, yeast, mold, animal, plant, and insect cells. However, in mass-producing target proteins in host cells, the cells recognize the target proteins as stress and thus produce molecular chaperones for their protection. The molecular chaperones are mostly heat shock proteins (HSPs) and present at least one in all cells.

In the case of *E. coli*, the HSPs include SecB, DnaK, DnaJ, GrpE, GroEL, GroES, IbpA, IbpB and the like, and play important roles in DNA duplication, RNA synthesis, protein synthesis, folding and recycling, and cell growth and division, etc. (LaRossa and Van Dyk, *Mol. Microbiol.,* 5, 529-34, 1991). The most typical HSPs in the cytoplasm of *E. coli* are Dnak-DnaJ-GrpE and GroEL-GroES. DnaK is bound to the hydrophobic fragment of a denatured protein and hydrolyzed by DnaJ, and then, DnaK is recycled by GrpE while restoring the denatured protein to a native protein. This folding of the denatured protein is accelerated by GroEL-GroES.

Many studies have been conducted in attempts to improve the production of target proteins using HSPs. Studies that had been conducted until now can be broadly divided into a method of producing target proteins in soluble form and a method of producing target proteins in insoluble inclusion body form. The former method is characterized in that HSPs are simultaneously expressed to improve the production and activity of target proteins. Goloubinoff et al. have reported that the production of active foreign ribulose bisphosphate carboxylases (ribulose) was improved by GroEL and GroES (Goloubinoff et al., *Nature,* 337, 44-7, 1989). Furthermore, Georgiou and Valax have reported the use of GroEL and GroES, or DnaK and DnaJ, in the production of β-galactosidase (Georgiou and Valax, *Curr. Opin. Biotechnol.,* 7, 190-7, 1996). In addition, Murby et al. have reported that the DnaK protein essential for the expression and secretion of cell's own proteins or target proteins was coexpressed with alkaline phosphatase or fusion proteins (Murby et al., *Biotechnol., Appl. Biochem.,* 14, 336-46, 1991).

However, this system has the following several problems in the production of target proteins: (1) since HSPs proteins are simultaneously expressed in excessive amounts, the ratio of HSPs proteins in total protein is increased to 30-50%, thereby relatively reducing a capability for cells to maximally synthesize target proteins, (2) since two expression vectors are used, the stability of plasmids is reduced, (3) since the exact folding of target proteins is achieved by the cooperative action of many different molecular chaperones, this folding cannot be achieved with one or two kinds of chaperones (Langer et al., *Nature,* 356, 683-9, 1992). Recently, in an attempt to solve some of such problems, there has been developed a method where strains having a mutant in HSPs themselves are used. Baneyx et al. have reported that the production of target proteins was increased 2-4 fold by the use of a DnaK mutant (U.S. Pat. No. 5,552,301).

Meanwhile, the latter method is characterized in that the production of target proteins is enhanced by the use of strains deficient in a regulator rpoH for HSPs. The rpoH gene (sigma 32, "$\delta^{32}$") mutant stains reduces the synthesis of HSPs involved in the folding and degradation of a denatured protein, and thus, are suitable for use in the production of proteins liable to be degreed by protease, or in producing target proteins in insoluble inclusion body form. Easton et al. have reported that bIGF2 (bovine insulin-like growth factor 2) as an inclusion body in the cytoplasm was produced at 20-25% by the use of the rpoH strains Easton et al., *Gene,* 101, 291-5, 1991). Moreover, Obukowicz et al. have reported that the production of target proteins was enhanced by using a new rpoH mutant strain (Obukowicz et al., *Appl. Environ. Microbiol.,* 58, 1511-23, 1992). In addition, Goldberg et al. have reported that the degradation of target proteins was reduced by using a rpoH and lon mutant strain, thereby enhancing the production of target proteins (U.S. Pat. No. 4,758,512). However, this system has a fatal effect on cell growth in producing target proteins.

Up until now there has been no use of small heat shock proteins (sHSPs) in the production of target proteins. sHSPs are HSPs with a small molecular weight of 12-42 kDa, and are induced by heat, or stress such as the overproduction of target proteins, and also protect the denaturation of target proteins. sHSPs are present in all organisms ranging from eukaryotes to prokaryotes, and sHSPs, which have been found until now, include human sHSPs (HSP27, α- and β-crystallin), murine HSP25, *Pisum sativum* (pea) HSP18.1, *Saccharomyces cerevisiae* HSP26, *Bradirhizobium japonicum* sHSPs (HSPH, HSPB, HSPC, HSPF), *Metlaznocoecus jannaschii* HSP16.5, *Synechococcus vulcanus* HSP16, and *Mycobacterium tuberculosi* HSP16.3 (Studer and Narberhaus, *J. Biol. Chem.,* 275, 37212-8, 2000).

Particularly, it was reported that ibpA and/or ibpB genes as inclusion body-associated proteins belonging to sHSPs binds to target proteins in producing target proteins in recombinant *E. coli* (Allen et al., *J. Bacteriol.,* 174, 6938-47, 1992). Thus, it is obvious that the ibpA and/or ibpB genes belonging to sHSPs protect denatured proteins by stress in organisms, particularly bacteria.

A method of secreting target proteins into *E. coli* periplasm or culture medium has the following several advantages: (1) since periplasm or medium contains proteins at significantly lower amounts than cytoplasm, target proteins can be isolated and purified at high purity (Nossal et al., *J. Biol. Chem.,* 241, 3055-62, 1966), (2) since target proteins secreted into periplasm or medium are isolated from cytoplasm where most of proteases exist the degradation of target proteins caused by cytoplasmic proteases can be prevented in advance, thereby increasing the yield of target proteins (Meerman and Georgiou, *Ann. NZ Acad. Sci.,* 721, 292-302, 1994), (3) since periplasm is a more oxidized environment than cytoplasm, disulfide binding is more easily made and thus the correct folding of produced proteins is achieved, thereby remarkably reducing the formation of an inclusion body (Hockney, *TIBTECH;* 12, 456-63, 1994). However, cases can also occur where no secretion of target proteins is made or the secreted proteins are inactive.

Meanwhile, it can be advantageous that any proteins are produced in insoluble inclusion body form. By this time, many studies on the production of an inclusion body were conducted, but the exact mechanism of inclusion body formation is not yet established and any general relation is not yet found (Makrides, S C, *Microbiol. Rev.,* 60, 512-38, 1996). The formation of the inclusion body varies depending on a host-vector system, and the characteristics, and culturing and expression conditions of proteins, and thus, can be found only by a test in the desired system.

Therefore, the present inventors have conducted extensive studies in an attempt to develop a strain system of increasing the production of target proteins using bacteria, and consequently, found that the use of bacteria from which ibpA and ibpB genes coding for inclusion body-associated proteins of *E. coli* were deleted provides an increase in secretory production and activity of target proteins, and the use of bacteria where the ibpA and/or ibpB genes coding for inclusion body-associated proteins of *E. coli* were amplified provides an increase in production of target proteins in the cytoplasm and also allows for the production of target proteins in inclusion body form. On the basis of these points, the present invention was perfected.

DISCLOSURE OF THE INVENTION

Accordingly, an object of the present invention is to provide ibpA and ibpB gene-deleted bacteria for the efficient secretion of target proteins, and a method for the secretory production of target proteins, which comprises culturing the said bacteria.

Another object of the present invention is to provide ibpA and/or ibpB gene-amplified bacteria, and a method for producing target proteins in insoluble inclusion body form, which comprises culturing the bacteria.

To achieve the above objects, the present invention provides ibpA and ibpB gene-deleted bacteria, and a method for the secretory production of target proteins, which comprises culturing the bacteria.

In the present invention, the bacteria are preferably *E. coli,* containing genes coding for target proteins, and additionally a signal sequence.

Moreover, the present invention provides plasmid pACTacIbpAB, pACIbpAB, pACTacIbpAB or pACTacIbpB, which is used to amplify ibpA and/or ibpB genes in bacteria.

Furthermore, the present invention provides a method for producing ibpA and/or ibpB gene-amplified bacteria, and a method for producing target proteins in insoluble inclusion body form, which comprises culturing the bacteria.

More specifically, the present invention provides bacteria where the ibpA and/or ibpB genes were amplified by transformation with the plasmid pACTacIbpAB, pACIbpAB, pACTacIbpA or pACTacIbpB.

In the present invention, the bacteria are preferably *E. coli,* and contain a gene coding for a target protein. Also, the ibpA and/or ibpB genes are amplified, so that target proteins, which have been produced in soluble form, can be produced in insoluble inclusion body form. The target proteins in inclusion body form are accumulated in the cytoplasm.

In addition, the present invention provides a method for regulating the production form of target proteins to soluble or insoluble form by deleting or amplifying the ibpA and/or ibpB genes.

Up till now there was no report on the effect of the ibpA and/or ibpB genes on the production of target proteins, and no use of the ibpA and/or ibpB genes in the production of target proteins. According to the present invention, the secretory production and activity of target proteins were enhanced by using bacteria from which the ibpA and ibpB genes coding for inclusion body-associated proteins of *E. coli* were deleted. In addition, the production of target proteins in the cytoplasm was increased and also the target proteins were produced in inclusion body form, by using bacteria where the ibpA and/or ibpB genes coding for inclusion body-associated proteins of *E. coli* was amplified.

In the present invention, since the formation of an inclusion body can be manipulated as one desires, many advantages as described below can be obtained according to the processing systems of proteins useful in medical and industrial fields and the characteristics of proteins: (1) the construction and culturing conditions of vectors are simple, and the high production of proteins can be achieved by a method, such as high cell density cultivation (Lee, S Y, *Trends Biotechnol.,* 14, 98-105, 1996), (2) since proteins are purified to a purity of generally 80-90% by low-speed centrifugation following cultivation, strain collection and destruction, they are isolated in a far easier manner than the case of soluble proteins that are isolated at a purity of 1-30% in this initial step (Jeong and Lee, *Appl. Environ. Microbiol.,* 65, 3027-32, 1999), (3) in the case of proteins which are sensitive to intracellular protease to cause their degradation, they can be protected from the attack of protease by the formation of an inclusion body (Kane and and Hartley, *Trends Biotechnol.,* 6, 95-101, 1988). In addition, since the solubilization and renaturation processes of an inclusion body are well established by experiments, obtaining proteins in inclusion body form can be a far better production system than obtaining the proteins in soluble form (Denefle et al., *Gene,* 56, 61-70, 1987; Saito et al., *J. Biochem.,* 101, 1281-88, 1987; Gill et al., *Bio/Technol.,* 3, 643-6, 1985; Weir and Sparks, *Biochem. J.,* 245, 85-91, 1987).

BRIEF DESCRIPTION OF THE DRAWINGS

In FIG. 1, ibpA' shows 500 bp from the 5' end at the front of an ibpA gene, and ibpB' shows 500 bp from the 3' end of an ibpB gene.

DETAILED DESCRIPTION OF THE INVENTION

Figure 1:
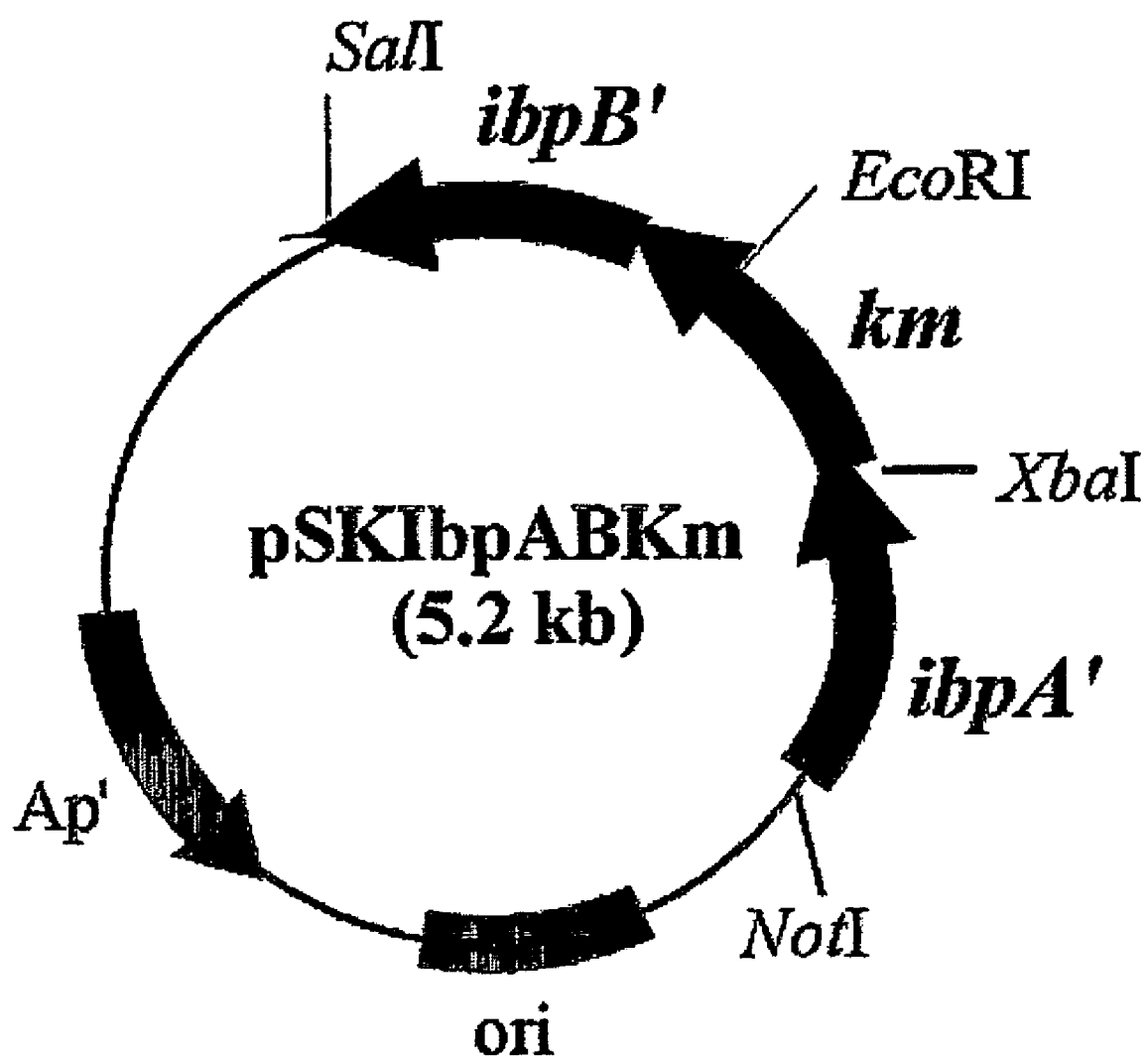
FIG. 1 is a gene map of plasmid pSKIbpABKm.

The present invention will hereinafter be described in further detail by examples. It will however be obvious to a person skilled in the art that the present invention is not limited by the examples.

EXAMPLE 1

Construction of ibpA, ibpB or ibpAB Gene-deleted Bacteria

The chromosomal DNA of *E. coli* W3110 (ATTC 39936) was isolated and purified according to a method described in Sambrook et al., *Molecular Cloning*, 2nd ed., Cold Spring Harbor Laboratory Press, NY, 1989. *E. coli* W3110 was cultured in 500 ml Luria-Bertani medium (LB medium) for 24 hours. The strain of early log phase was collected by centrifugation, and then, suspended in 50 ml TE solution (10 mM Tris, 1 mM EDTA; pH 7.6) containing 10 mg/ml lysozyme (Sigma Co., USA). The strain suspension was cultured at room temperature for 24 hours with slow stirring.

In order to destruct the strain and remove proteins, the culture solution was added with 16 ml of 10% SDS (sodium dodecyl sulfate) solution and 570 μl of 20 mg/ml Proteinase K (Sigma Co., USA), followed by reaction at 37° C. for one hour. Next 14 ml of 0.5 M NaCl solution and 10.66 ml of 10% cetyltrimethylammoniumbromide (CTAB; Sigma Co., USA) in 0.7 M NaCl solution were added and then reacted at 65° C. for 10 minutes. After this, chloroform-isopropyl alcohol (24:1) of the same volume as the reaction solution was added to the reaction solution and carefully mixed at room temperature for 2 hours. The mixed solution was centrifuged at 6,000 rpm for 10 minutes, and the supernatant was transferred into a beaker, to which cooled ethanol was added slowly at 2-fold larger volume than the supernatant to precipitate chromosomal DNA. The precipitated DNA was rolled up around a glass rod. The glass rod was air-dried to remove ethanol, and the chromosomal DNA was dissolved in 1 ml TE solution. RNase was added to the DNA solution to a final concentration of 50 g/ml, followed by reaction at 37° C. for one hour.

At the end of the reaction, chloroform-isoamylalcohol (24:1) of the same volume as the reaction solution was added, and carefully mixed at room temperature for 2 hours. The mixed solution was centrifuged at 6,000 rpm for 10 minutes, and the supernatant was transferred into a beaker, to which cooled ethanol was added slowly at 2-fold larger volume than the supernatant to precipitate chromosomal DNA. The precipitated DNA was rolled up around a glass rod. The glass rod was air-dried to remove ethanol, and finally, the chromosomal DNA of purified *E. coli* W3110 was dissolved in 1 ml TE solution.

For the deletion of an ibpA, ibpB or ibpAB gene from *E. coli*, the red operon of bacteriophage λ was used (Jeong and Lee, *Appl. Environ. Microbiol.*, 68, 4979-85, 2002). For the construction of a mutant using homologous recombination, *E. coli* W3110 was transformed with pTrcEBG containing the red operon of bacteriophage λ, and then added with 1 mM IPTG to induce the expression of red operon in *E. coli* W3110 (transformed with pTrcEBG). Using this *E. coli*, an electroporation-competent cell was prepared.

For the construction of a mutant using allogenic recombination, the chromosomal DNA of *E. coli* W3110 was used as a template. Primers of SEQ ID NOs: 1 and 2 were used to amplify a promoter-containing 500 bp fragment of an ibpAB gene, and primers of SEQ ID NOs: 3 and 4 were used to amplify a 500 bp fragment from the 3' end of the ibpAB gene. The amplified gene was cloned into the NotI restriction enzyme and XbaI recognition sites of pBluescript SK(−)(Stratagene Cloning Systems, USA), and the EcoRI restriction enzyme and SalI recognition sites of pBluescript SK(−), respectively Primers of SEQ ID NOs: 5 and 6 were used to amplify the 600 bp fragment of a kanamycin-resistant gene, and the amplified gene was cloned into the XbaI restriction enzyme and the EcoRI recognition sites at the middle of the plasmid produced as described above, thereby obtaining plasmid pSKIbpABKm (FIG. 1).

A PCR product obtained with the primers of SEQ ID NOs: 1 and 4 using plasmid pSKIbpABKm as a template was transformed into the electroporation-competent cell constructed as described above, thereby deleting the ibpA and ibpB genes. This mutant *E. coli* from which the ibpA and ibpB genes had been deleted was termed WIB101. A chromosome was isolated from the WIB101 strain, and then the insertion of a kanamycin-resistant gene into the location of the ibpAB gene in the chromosome was confirmed by a PCR method with the primers of SEQ ID NOs: 5 and 6.

Furthermore, in order to make *E. coli* where the ibpA or ibpB gene was deleted, kanamycin-resistant genes, which contain 60 bp from the 5' end of the ibpA or ibpB gene and 60 bp from the 3' end of the ibpA or ibpB gene, respectively, were amplified by PCR with primers of SEQ ID NOs: 7 and 8, and primers of SEQ ID NOs: 9 and 10, respectively. The amplified PCR products were transformed into the electroporation-competent cell, thereby deleting the ibpA or ibpB gene. The mutant *E. coli* from which the ibpA or ibpB gene had been deleted were termed WIbpA and WIbpB, respectively.

All the PCRs consisted of initial denaturation at 95° C. for 5 minutes; 30 cycles of denaturation at 95° C. for 50 seconds, annealing at 55° C. for one minute, and extension at 72° C. for one minute and 30 seconds; and final extension at 72° C. for 5 minutes.

(SEQ ID NO: 1)
5'-ataagaatgcggccgccagctgtggatcaccgaaactgat-3'

(SEQ ID NO: 2)
5'-gctctagatgcatagactgaggggcagca-3'

(SEQ ID NO: 3)
5'-ggaattctttcgactgtttaagatatttcgg-3'

(SEQ ID NO: 4)
5'-acgcgtcgacggagaaaatccccagcactaccgg-3'

(SEQ ID NO: 5)
5'-gctctagagccacgttgtgtctcaaa-3'

(SEQ ID NO: 6)
5'-cgaattcttagaaaaactcatcgagca-3'

(SEQ ID NO:7)
5'-atgcgtaactttgatttatcccgctttaccgttctgctattggatt tgaccgtttgtttgccacgttgtgtctcaaaat ctc-3'

(SEQ ID NO: 8)
5'-tgcgtaacttcgatttatccccactgatgcgtcaatggatcggtttt gacaaactggccgccacgttgtgtctcaa-3'

(SEQ ID NO: 9)
5'-tgcgtaacttcgatttatccccactgatgcgtcaatggatcggtttt gacaaactggccgccacgttgtgtctcaa-3'

(SEQ ID NO: 10)
5'-ttagctatttaacgcgggacgttcgctgatagcgatacgctgcgctg cgatgggttcaggttagaaaaactcat-3'

EXAMPLE 2

Construction of Recombinant Plasmid in which ibpA and/or ibpB Genes were Introduced In order to express ibpA and ibpB genes, recombinant plasmids were constructed as follows.

Using the chromosomal DNA of *E. coli* W3110 as a template, PCRs were conducted with primers of SEQ ID NOs: 11 and 12, primers of SEQ ID NOs: 13 and 14, and primers of SEQ ID NOs: 15 and 16, as described in Example 1, thereby obtaining ibpA, ibpB and ibpAB genes, respectively. Each of the obtained ibpA, ibpB and ibpAB genes was cloned into recombinant plasmid pTac99A digested with EcoRI and HindIII, thereby constructing plasmids pTac99IbpA, pTac99IbpB and pTac99IbpAB, respectively. Recombinant plasmid pTac99A was obtained as follows: The trc promoter of pTrc99A (Pharmacia Biotech., Uppsala, Sweden) was converted into the tac promoter of pKK223-3 (Pharmacia Biotech., Uppsala, Sweden). The tac promoter of pKK223-3 was digested with restriction enzymes PvuII and EcoRI, and then the gene fragment of the tac promoter was cloned into pTrc99A digested with the same restriction enzymes.

Figure 2:
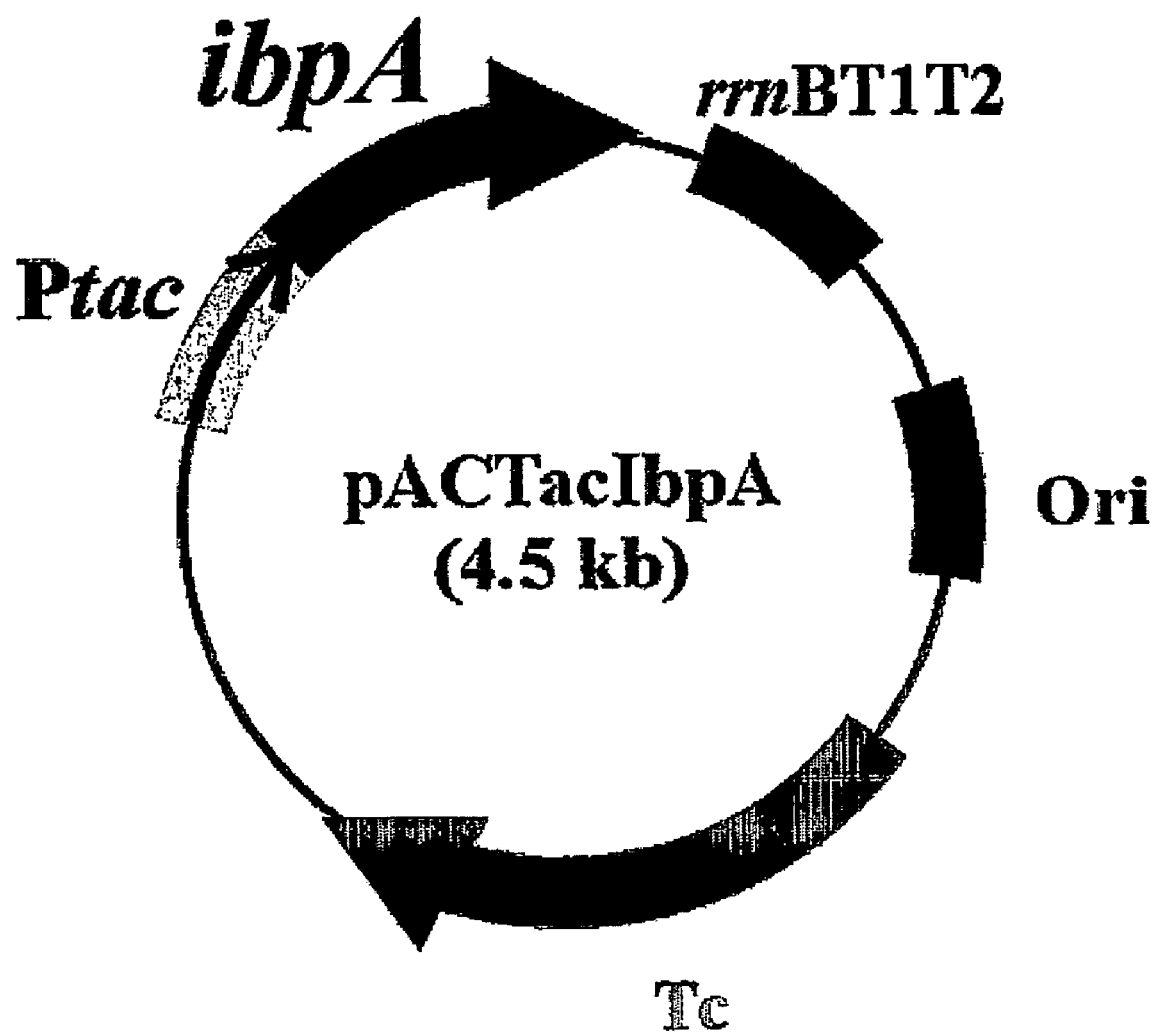
FIG. 2 is a gene map of plasmid pACTacIbpA.
Figure 3:
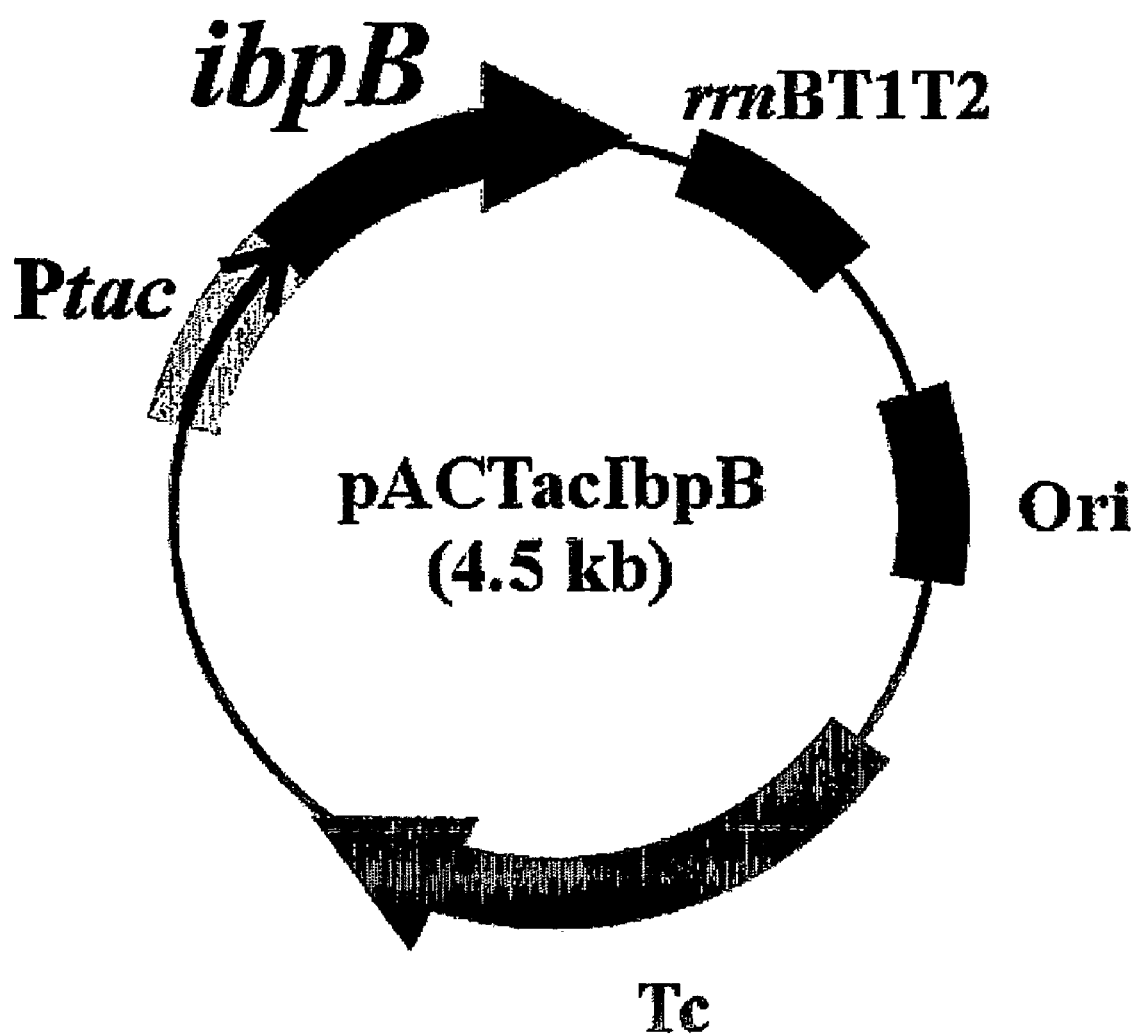
FIG. 3 is a gene map of plasmid pACTacIbpB.
Figure 4:
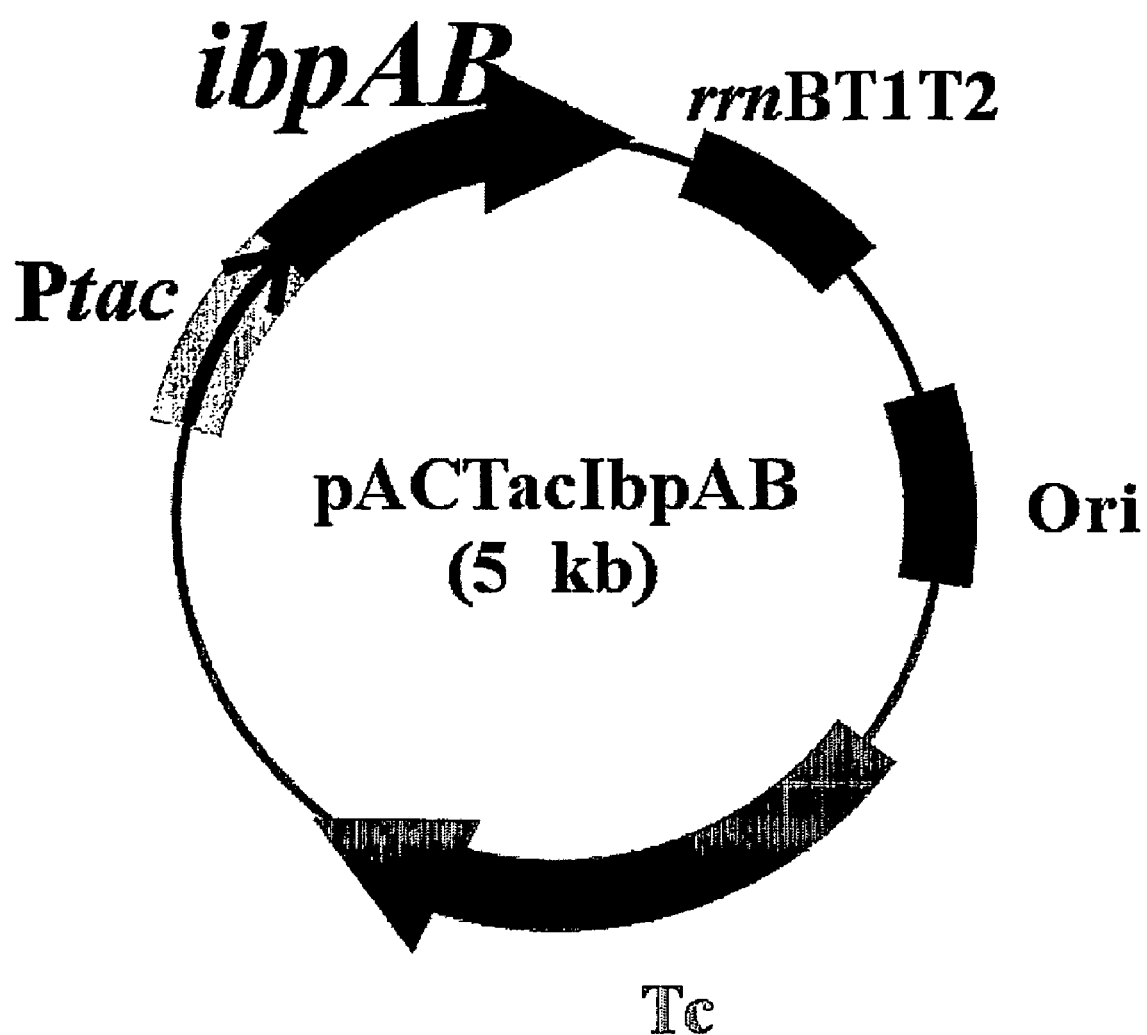
FIG. 4 is a gene map of plasmid pACTacIbpAB.

Each of plasmids pTac99IbpA, pTac99IbpB and pTac99IbpAB was digested with restriction enzymes SspI, and cloned into plasmid pACYC184 (New England Biolabs, USA) digested with DraI and PvuII, thereby constructing plasmids pACTacIbpA, pACTacIbpB and pACTacIbpAB, respectively (FIGS. 2, 3 and 4).

Figure 5:
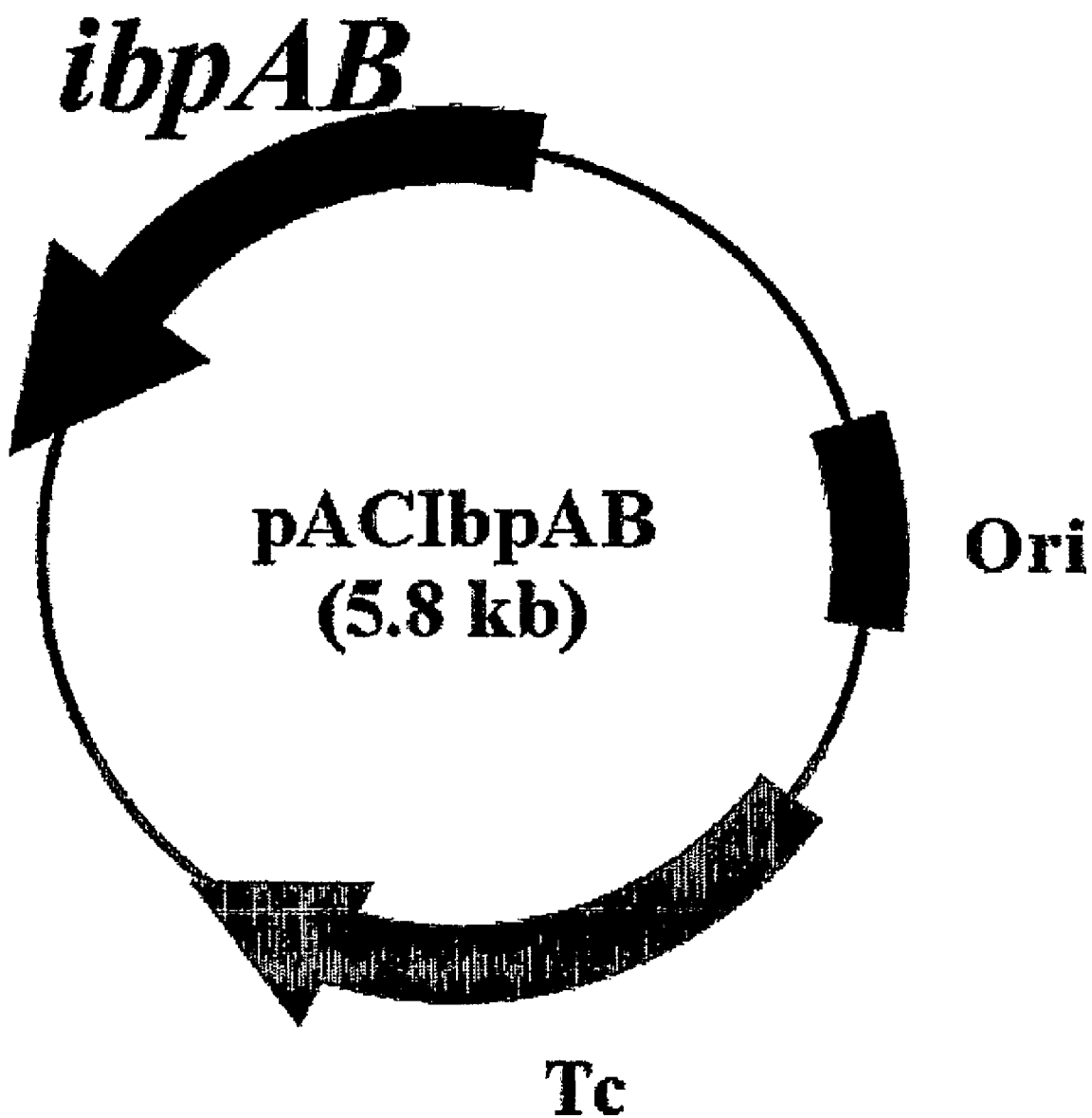
FIG. 5 is a gene map of plasmid pACIbpAB.

In order to express the ibpAB gene having a self-promoter, PCR was conducted as in Example 1, using the chromosomal DNA of W3110 as a template and primers of SEQ ID NOs: 17 and 18, thereby obtaining PCR products containing the ibpAB promoter and gene. The obtained gene was digested with EcoRI and cloned into pACYC184 (New England Biolabs, USA) digested with the same enzyme, thereby constructing plasmid pACIbpAB (FIG. 5).

(SEQ ID NO: 11)
5'-ggaattcatgcgtaactttgatttatccc-3'

(SEQ ID NO: 12)
5'-cccaagcttttagttgatttcgatacggcgc-3'

(SEQ ID NO: 13)
5'-ggaattcatgcgtaacttcgatttatccccactg-3'

(SEQ ID NO: 14)
5'-cccaagcttttagctatttaacgcgggacgttcgct-3'

(SEQ ID NO: 15)
5'-ggaattcatgcgtaactttgatttatccc-3'

(SEQ ID NO: 16)
5'-cccaagcttttagctatttaacgcgggacgttcgct-3'

(SEQ ID NO: 17)
5'-ggaattccagctgtggatcaccgaaactg-3'

(SEQ ID NO: 18)
5'-ggaattcagaacgtgccgaaatatctta-3'

EXAMPLE 3

Figure 6:
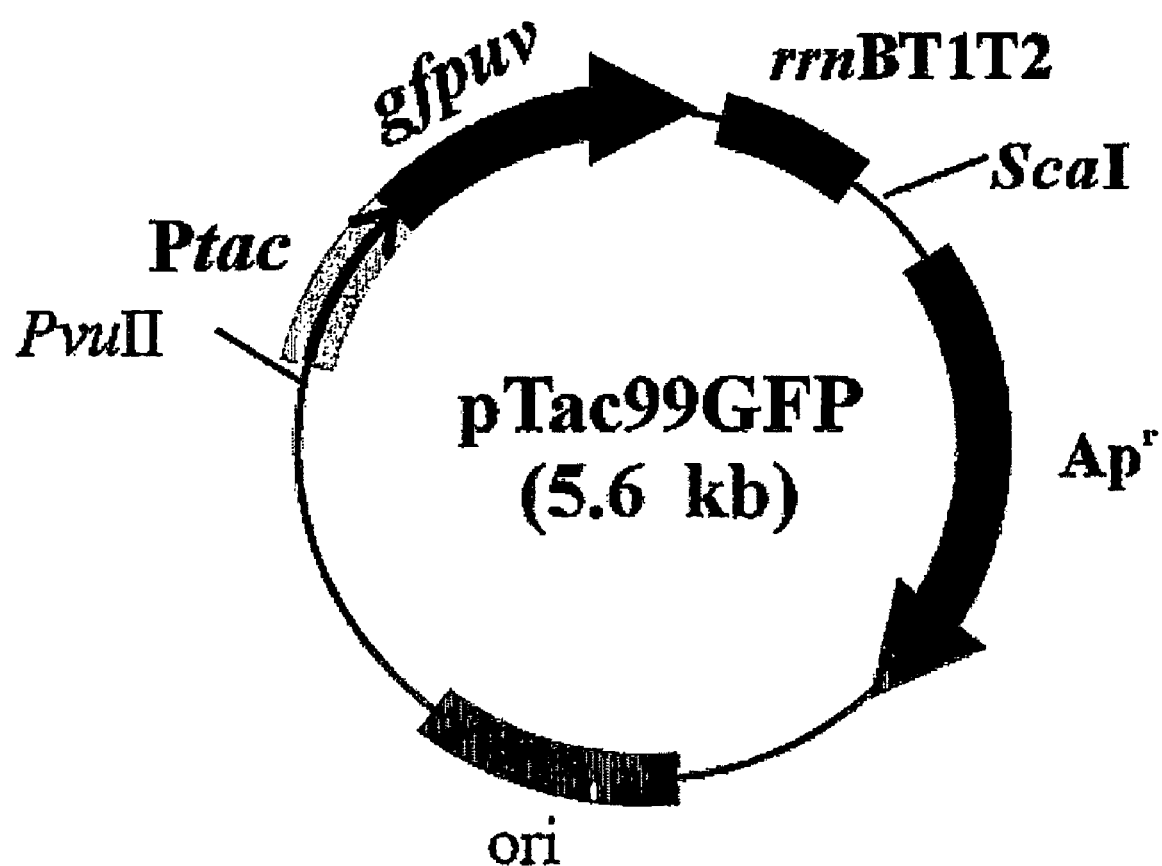
FIG. 6 is a gene map of plasmid pTac99GFP.

Construction of Recombinant Plasmid in which Gene of Target Protein was Introduced In order to express GFP (green fluorescent protein) of *Aequorea victoria*, PCR was conducted in the same manner as Example 1, using plasmid pGFP$_{uv}$ (Stratagene Cloning Systems, USA) as a template and primers of SEQ ID NOs: 19 and 20, thereby obtaining a GFP gene. The obtained GFP gene was digested with restriction enzymes EcoRI and HindIII, and cloned into plasmid pTac99A digested with the same enzymes, thereby constructing plasmid pTac99GFP (FIG. 6).

Figure 7:
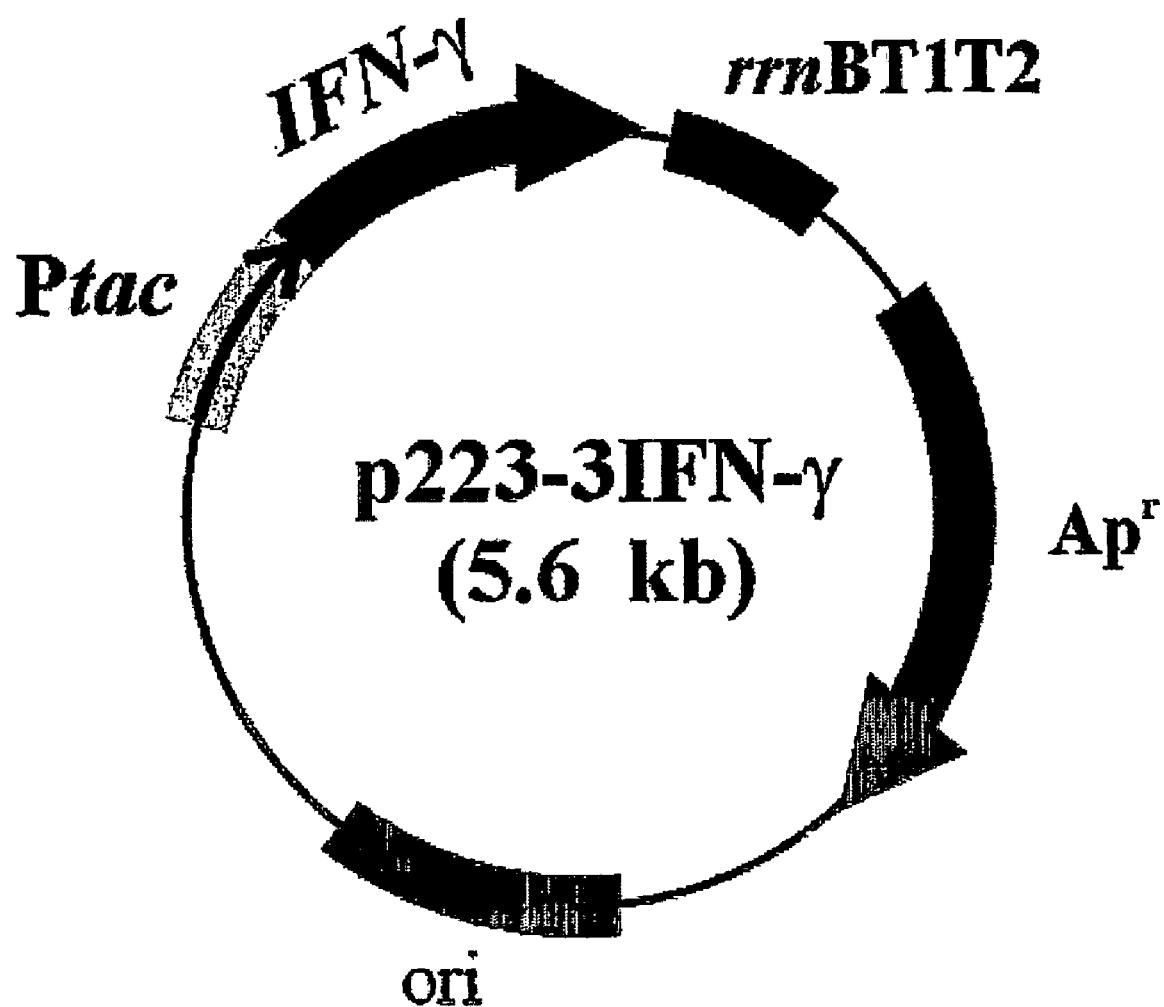
FIG. 7 is a gene map of plasmid p223-3IFN-γ.

For the expression of INF-γ (interferon-γ) protein, PCR was conducted in the same manner as Example 1, using plasmid pUC18/IFN-γ containing a human INF-γ gene obtained from the Cytokine Bank (http://cytokine.chonbuk.ac.kr/) as a template, and primers of SEQ ID NOs: 21 and 22, thereby obtaining an INF-γ gene. The obtained INF-γ gene was digested with restriction enzymes EcoRI and HindIII, and cloned into pKK223-3 (Pharmacia Biotech., Uppsala, Sweden) digested with the same enzymes, thereby constructing plasmid p223-3IFN-γ (FIG. 7).

Figure 8:
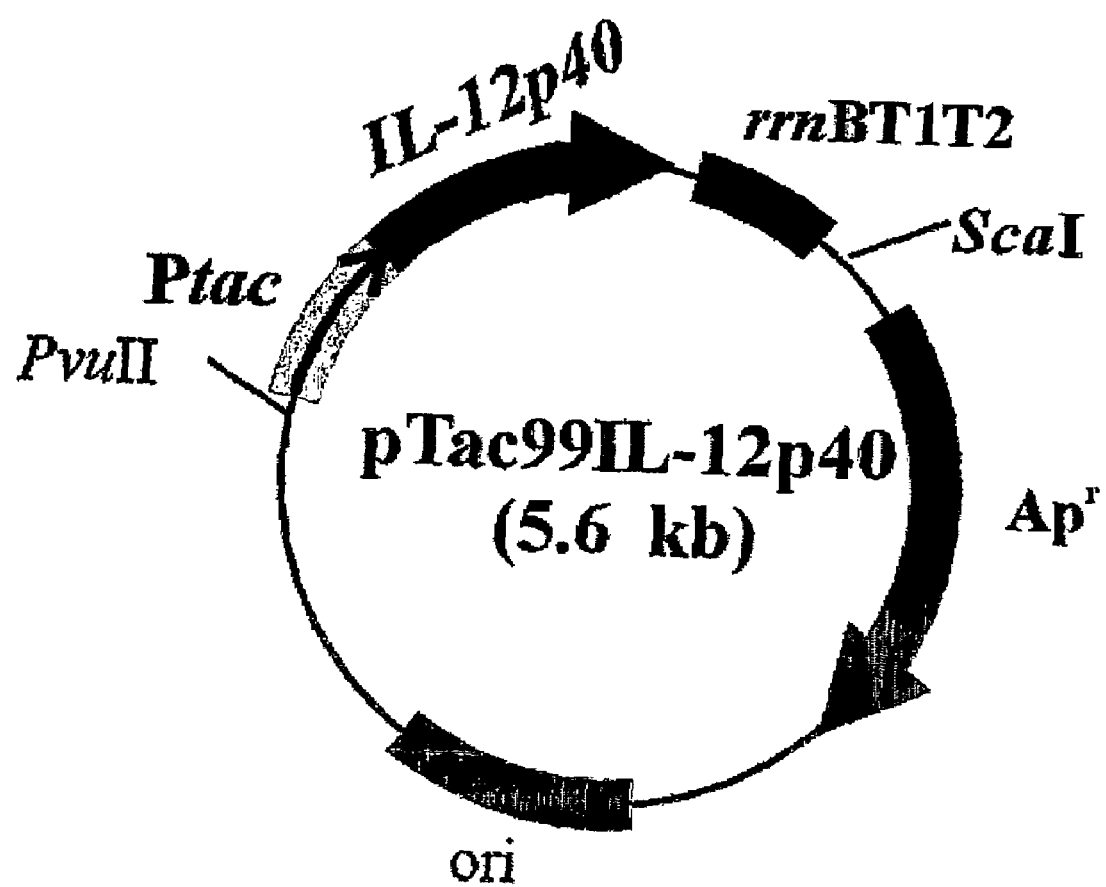
FIG. 8 is a gene map of plasmid pTac99IL-12p40.

For the expression of interleukin 12 β chain (IL-12p40) protein, PCR was conducted in the same manner as in Example 1, using plasmid pUC18/p40 containing a human interleukin β chain gene obtained from the Cytokine Bank (via the internet website at hypertext transfer protocol address cytokine.chonbuk.ac.kr) as a template, and primers of SEQ ID NOs: 19 and 20, thereby obtaining an IL-12p40 gene. The obtained IL-12p40 gene was digested with restriction enzymes EcoRI and HindIII, and cloned into pTac99A digested with the same enzyme, thereby constructing plasmid pTac99IL12p40 (FIG. 8).

```
                                              (SEQ ID NO: 19)
5'-ggaattcatgagtaaaggagaagaactttt-3'

(SEQ ID NO: 20)
5'-cccaagctttatttgatgagctcatcc-3'

(SEQ ID NO: 21)
5'-ggaattcatgtgttactgccaggacccatat-3'

(SEQ ID NO: 22)
5'-cccaagcttttactgggatgctcttcgacc-3'
```

EXAMPLE 4

Secretory Production of Alkaline Phosphatase Protein in ibpA and ibpB-Deleted *E. coli*

Each of *E. coli* WIbpA, WIbpB, WIB101 constructed in Example 1 and parent strain W3110 was transformed with the existing alkaline phosphatase-expressing plasmid pTrcS1PhoA (Choi et al., *Appl. Microbiol. Biotechnol.*, 53, 640-5, 2000). Each of the transformed strains was screened on a plate containing kanamycin and ampicillin or only ampicillin. The respective recombinant *E. coli* strains were cultured in LB medium at 37° C. The expression of alkaline phosphatase protein was induced by adding 1 mM IPTG (isopropyl-β-thiogalactoside) at an optical density (O.D.) of 0.7 as measured with a spectrophotometer at a 600 nm wavelength. At 4 hours after induction, 1 ml of each of the culture solutions was taken and fractionated into total, soluble, insoluble, periplasmic and cytoplasmic protein, and at the same time, 0.1 ml of each of the culture solutions was taken and measured for alkaline phosphatase activity.

The fractionation of the respective culture solutions into total, soluble, insoluble, periplasmic and cytoplasmic protein was carried out as follows: For total protein, 1 ml of culture solution was centrifuged at 4° C. and 6,000 rpm for 5 minutes, the obtained precipitate was washed one time with 0.5 ml TE solution and centrifuged 4° C. and 6,000 rpm for 5 minutes to obtain a precipitate. The precipitate was suspended in 0.2 ml TE solution and subjected to ultrasonic homogenization, thereby obtaining total protein. For fractionation into soluble and insoluble protein, the total protein was centrifuged at 4° C. and 10,000 rpm for 10 minutes, and the supernatant was collected as a soluble protein and the precipitate as an insoluble inclusion body.

For fractionation into periplasmic and cytoplasmic protein, 1 ml of the culture solution was centrifuged at 4° C. and 6,000 rpm for 5 minutes, and the obtained precipitate was added with 0.4 ml of 30 mM Tris-HCl solution (pH 8.0) containing 20% sucrose, sufficiently mixed, added with 1 mM EDTA and then stirred at room temperature for about 10 minutes. Then, the stirred mixture was centrifuged at 4° C. and 10,000 rpm for 10 minutes, and the obtained precipitate was added with 0.4 ml of cool 5 mM $MgSO_4$ solution, carefully mixed, stirred in ice for 10 minutes, centrifuged at 4° C. and 10,000 rpm for 10 minutes, and the supernatant and precipitate were collected separately. In this case, the supernatant was collected as a periplasmic protein, and the precipitate was suspended in 0.2 ml TE buffer solution, homogenized with ultrasonic waves, and collected as a cytoplasmic protein (Ausubel et al., *Current Protocols in Molecular Biology*, 1989).

200 μl of each of the protein containing solutions produced as described above was taken, mixed with 50 μl SDS-PAGE sample solution (25% glycerol, 2% SDS, 14.4 mM 2-mercaptoethanol, 0.1% bromophenol blue, 60 mM Tris-HCl), boiled for 10 minutes, and then subjected to SDS-PAGE gel electrophoresis on a 12% separating gel. Next the gel was immersed in staining solution (40% methanol, 10% acetic acid, 0.25 g/L Coomassie brilliant blue R) for at least two hours to stain the gel, and immersed two times in de-staining solution for at least two hours a time to de-stain the gel (FIG. 9).

Figure 9:
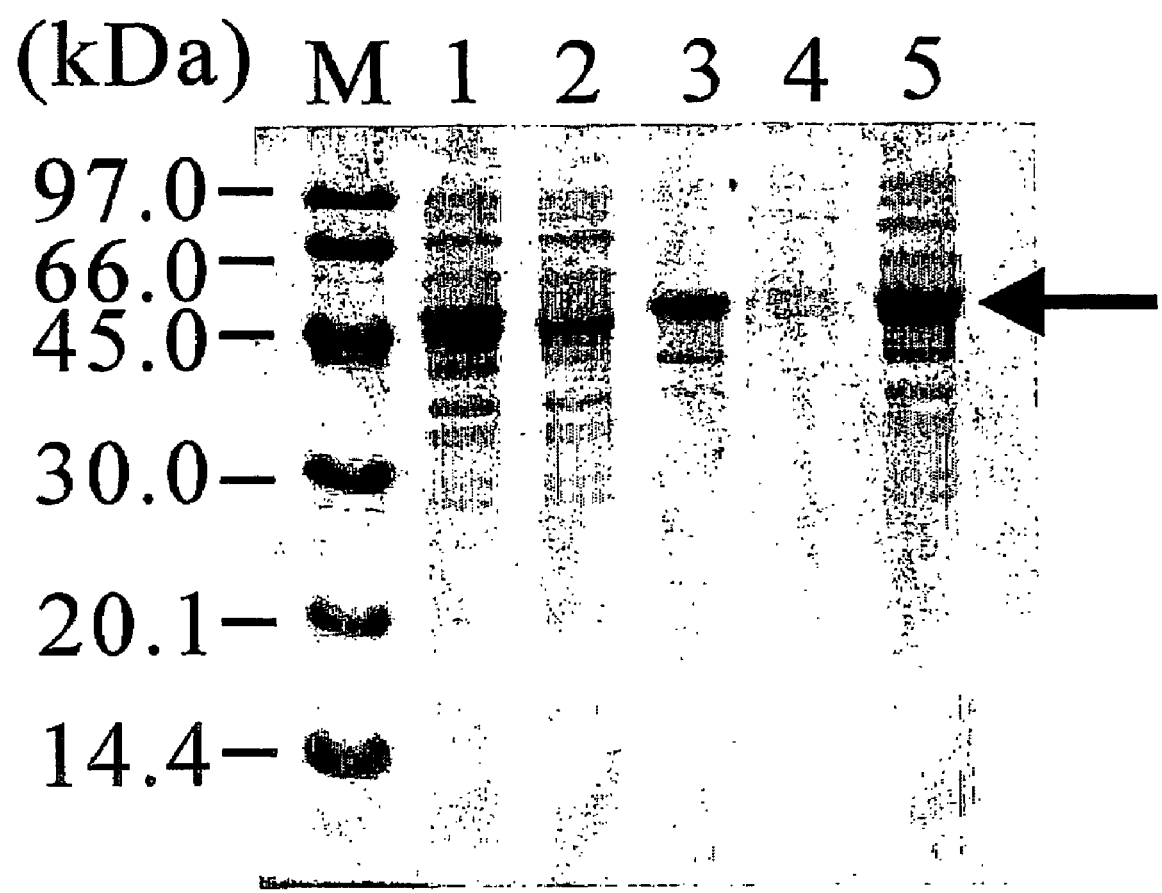
FIG. 9 is an electrophoretic picture showing the result of SDS-PAGE analysis of proteins, which were obtained from recombinant *E. coli* W3110 transformed with recombinant plasmid pTrcS1PhoA, at 4 hours after induction.

FIG. 9 is an electrophoretic picture showing the result of SDS-PAGE analysis of proteins obtained from recombinant *E. coli* W3110 transformed with pTrcS1PhoA. In FIG. 9, lane M shows the molecular mass standard, and lanes 1-5 show total protein, soluble protein, insoluble protein, periplasmic protein and cytoplasmic protein, respectively, which were obtained from the transformed strain at 4 hours after the induction of expression. Also, the left arrow(←) shows alkaline phosphatase protein.

As shown in FIG. 9, most of alkaline phosphatase in *E. coli* W3110 was present in insoluble inclusion body form, and N-terminal sequence analysis for this protein showed that a signal sequence was present in an uncleaved form and not secreted into periplasm. In addition, the result of the SDS-PAGE gel electrophoresis was used for the quantification of proteins using a densitometer, and as a result, the ratio of alkaline phosphatase in total protein was about 15%.

Figure 10:
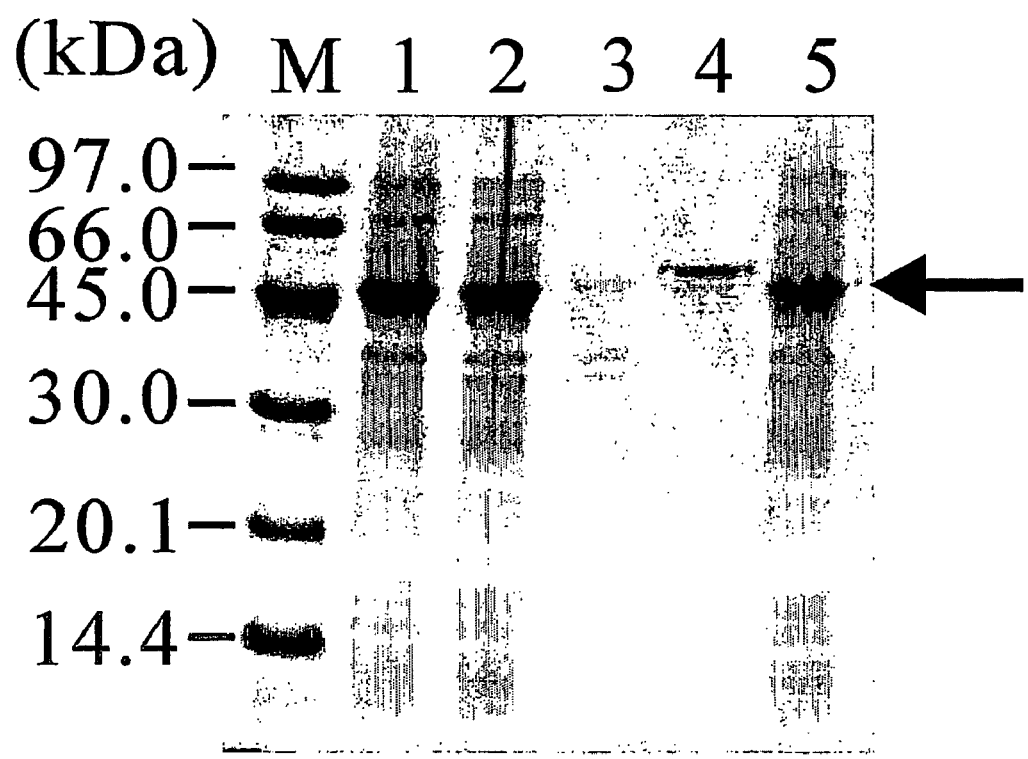
FIG. 10 is an electrophoretic picture showing the result of SDS-PAGE analysis of proteins obtained from recombinant *E. coli* WIbpA and WIbpB transformed with recombinant plasmid pTrcS1PhoA.

FIG. 10 is an electrophoretic picture showing the result of SDS-PAGE gel electrophoresis of proteins obtained from recombinant *E. coli* WIbpA and WIbpB transformed with recombinant plasmid pTrcS1PhoA. In FIG. 10, lane M shows the molecular mass standard, and lanes 1-3 show total protein, soluble protein and insoluble protein, respectively, which were obtained from the transformed strain WIbpA at 4 hours after the induction of expression. Lanes 4-6 show total protein, soluble protein and insoluble protein, respectively, which were obtained from the transformed strain WIbpB at 4 hours after the induction of expression. Also, the left arrow(←) shows alkaline phosphatase protein.

As shown in FIG. 10, most of alkaline phosphatase in *E. coli* WIbpA and WIbpB was present in insoluble inclusion body form, and N-terminal sequence analysis for this protein showed that a signal sequence was present in an uncleaved form and not secreted into periplasm.

Figure 11:
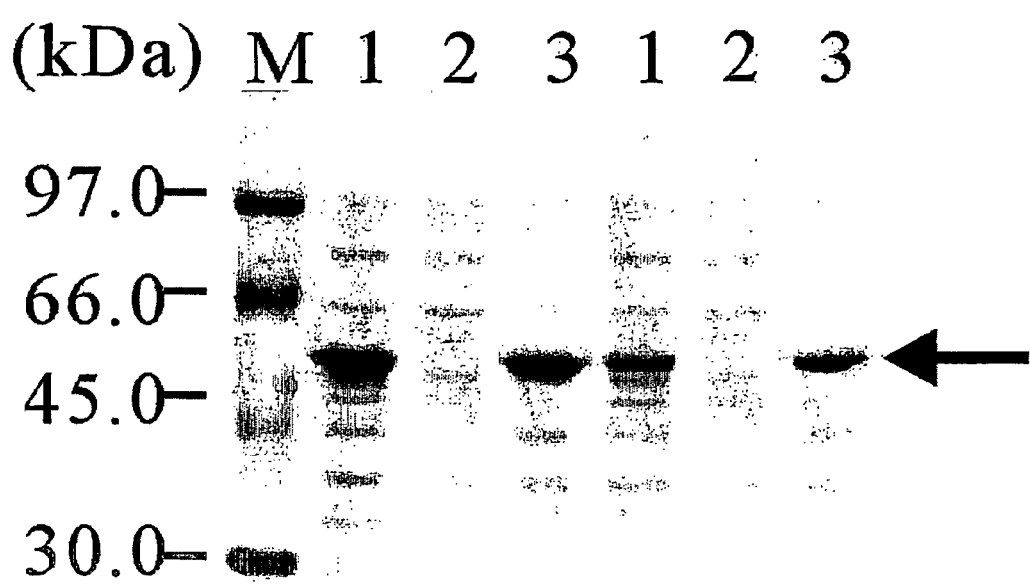
FIG. 11 is an electrophoretic picture showing the result of SDS-PAGE analysis of proteins, which were obtained from recombinant *E. coli* WIB101 transformed with recombinant plasmid pTrcS1PhoA, at 4 hours after induced expression.

FIG. 11 is an electrophoretic picture showing the result of SDS-PAGE analysis of proteins obtained from recombinant *E. coli* WIB101 transformed with recombinant plasmid pTrcS1PhoA. In FIG. 9, lane M shows the molecular mass standard, and lanes 1-5 show total protein, soluble protein, insoluble protein, periplasmic protein and cytoplasmic protein, respectively, which were obtained from the transformed stain at 4 hours after the induction of expression. Also, the left arrow(←) shows alkaline phosphatase protein.

As shown in FIG. 11, it could be found that most of alkaline phosphatase whose secretion signal sequence had been cleaved after secretion in *E. coli* WIB101 was present in a soluble alkaline phosphatase form, and thus the amount of soluble alkaline phosphatase contained in periplasm was relatively high. In addition, the result of the SDS-PAGE gel electrophoresis was used for the quantification of proteins using a densitometer, and as a result, the ratio of secreted alkaline phosphatase in total protein was about 30%, indicating that alkaline phosphatase was mostly secreted into periplasm.

The activity of secreted alkaline phosphatase was measured by the following method (Brickman and Beckwith, *J. Mol. Biol.*, 96, 307-16, 1975). *E. coli* obtained as described above was suspended in 1 ml of 50 mM Tris-HCl solution (pH 7.5), and added with 0.1 ml chloroform, followed by reaction at 37° C. for 5 minutes. Then, 0.1 ml of 0.4% PNPP (p-nitrophenyl phosphate) was added to the mixture, and reacted at 37° C. for 5 minutes. After the reaction was stopped with 0.1 ml of 1M $K_2HPO_4$ solution, the resulting solution was centrifuged at 12,000 rpm for 5 minutes and only the supernatant was collected. The supernatant was diluted in 50 mM Tris-HCl solution, and measured for its absorbance with a spectrophotometer at two wavelengths of 420 nm and 550 nm. The alkaline phosphatase activity (U/ml) was calculated according to the following equation, and the calculated results are given in Table 1 below:

$$\text{Activity} = 1000 \times \frac{(\text{Abs}_{420\,nm} - 1.75 \times \text{Abs}_{550\,nm})}{[\text{ReactionTime}(\text{min}) \times \text{ReactionVolume}(\text{ml}) \times O.D.]}$$

In Table 1, as controls, alkaline phosphatase activity in the culture solutions of *E. coli* W3110, WIbpA, WIbpB and WIB101 transformed with plasmid pJS101ΔP was measured as described above.

TABLE 1

Alkaline phosphatase activity in recombinant *E. coli* strains

| *E. coli* strains | Alkaline phosphatase activity (U/ml) |
| --- | --- |
| *E. coli* W3110 transformed with pJS101ΔP | 23 |
| *E. coli* W3110 transformed with pTrcS1PhoA | 1406 |
| *E. coli* WIB101 transformed with pJS101ΔP | 22 |
| *E. coli* WIB101 transformed with pTrcS1PhoA | 4720 |
| *E. coli* WIbpA transformed with pJS101ΔP | 25 |
| *E. coli* WIbpA transformed with pTrcS1PhoA | 1025 |
| *E. coli* WIbpB transformed with pJS101ΔP | 22 |
| *E. coli* WIbpB transformed with pTrcS1PhoA | 1790 |

As evident from Table 1 above, the alkaline phosphatase activity of *E. coli* WIB101 transformed with plasmid pTrcS1PhoA was at least 3 times higher tan *E. coli* W3110, WIbpA and WIbpB transformed with plasmid pTrcS1PhoA, and *E. coli* W3110, WIbpA, WIbpB and WIB101 transformed with pJS101ΔP as a control showed little or no alkaline phosphatase activity. Thus, considering the fact that alkaline phosphatase has no activity in the cytoplasm but has activity only when secreted into periplasm, it could be found that alkaline phosphatase produced in recombinant *E. coli* WIB101 transformed with the plasmid was successfully secreted into periplasm.

However, alkaline phosphatase produced in recombinant *E. coli* W3110, WIbpA and WIbpB was formed as an insoluble inclusion body without secretion into periplasm. Thus, in recombinant *E. coli* WIB101 transformed with the plasmid, alkaline phosphatase was mostly present in soluble form, and also alkaline phosphatase activity was significantly high. Moreover, since the cell concentration of recombinant *E. coli* WIB101 transformed with the plasmid was at least 2 times higher than recombinant *E. coli* W3110, the alkaline phosphatase activity of this recombinant *E. coli* WIB101 is at least 6 times higher than the recombinant *E. coli* W3110. Thus, it could be found that ibpA and ibpB-deleted *E. coli* WIB101 was a strain effective for the secretory production of soluble and active alkaline phosphatase.

EXAMPLE 5

Secretory Production of Human Leptin in ibpA and ibpB-Deleted *E. coli*

Each of *E. coli* WIB101 constructed in Example 1 and parent strain W3110 was transformed with the prior leptin expression plasmid pTrcSOb4 (Jeong and Lee., *Biotechnol. Bioeng.*, 67, 398-407, 2000). The transformed strains were subjected to cell cultivation in the same manner as in Example 4. The expression of leptin protein was induced by adding 1 mM IPTG at absorbance of 0.7 as measured with a spectrophotometer at a 600 nm wavelength. At 4 hours after the induction of expression, 1 ml of each of the culture solutions was taken, and fractionated into total protein, soluble protein and inclusion body protein (FIG. 12).

Figure 12:
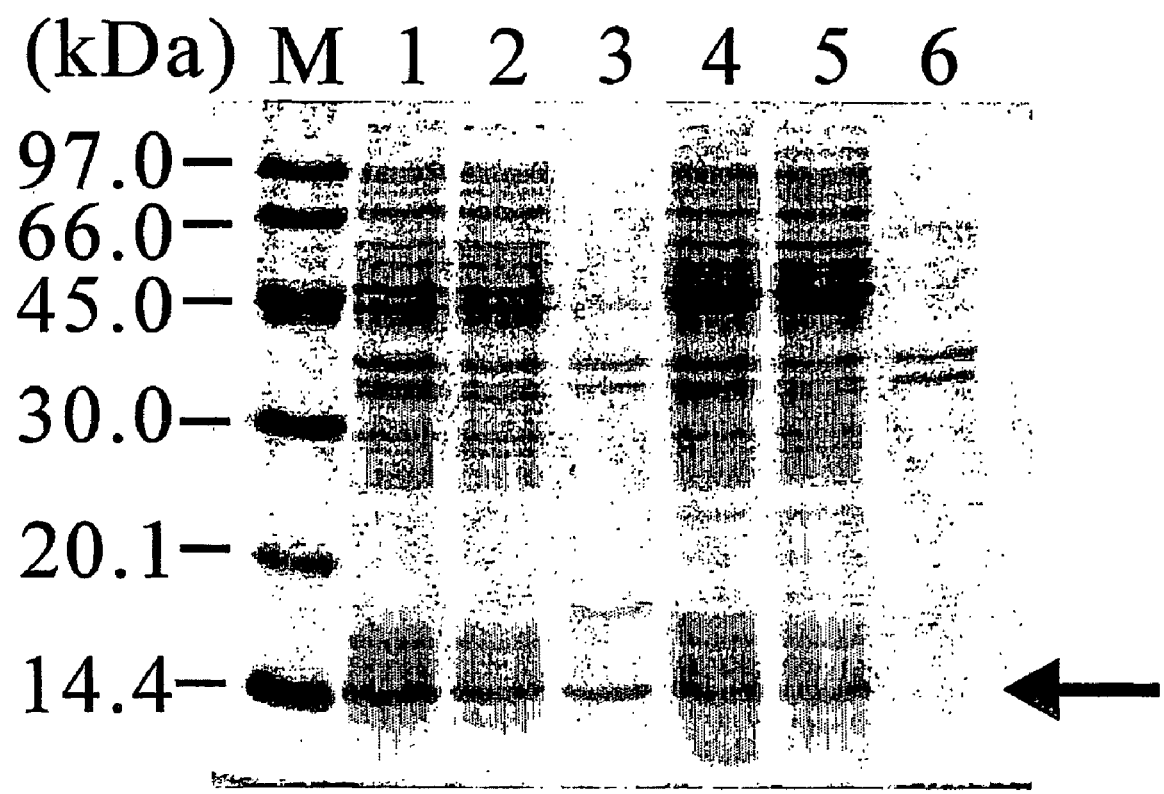
FIG. 12 is an electrophoretic picture showing the result of SDS-PAGE analysis of proteins, which were obtained from recombinant *E. coli* W3110 and WIB101 transformed with recombinant plasmid pTrcSOb4, at 4 hours after induced expression.

FIG. 12 is an electrophoretic picture showing the result of SDS-PAGE analysis of proteins obtained from recombinant *E. coli* W3110 and WIB101 transformed with plasmid pTrcSOb4. In FIG. 12, lane M shows the molecular mass standard, lanes 1-3 show total protein, soluble protein and insoluble protein, respectively, which were obtained from the transformed *E. coli* W3110 at 4 hours after the induction of expression. Lanes 4-6 represent total protein, soluble protein and insoluble protein, respectively, which were obtained from the transformed *E. coli* WIB101 at 4 hours after the induction of expression. Also, the left arrow(←) shows secreted human leptin protein.

As shown in FIG. 12, in the transformed *E. coli* W3110, about 50% of total leptin protein was formed as an insoluble inclusion body, but in the transformed *E. coli* WIB101, leptin protein was mostly formed as soluble protein. Moreover, the cell concentration of the transformed *E. coli* WIB101 was 3 times higher than the transformed *E. coli* W3110, and thus, the soluble leptin concentration of the transformed *E. coli* WIB101 was actually at least 3 times higher than the transformed *E. coli* W3110. Thus, it could be found that the ibpA and ibpB-deleted *E. coli* WIB101 was a strain effective for the secretory production of soluble leptin protein.

EXAMPLE 6

Production of Human IGF-I (Insulin-Like Growth Factor) Protein in the Cytoplasm Using IbpA and/or IbpB Expression System

*E. coli* WIB101, WIbpA and WIbpB constructed in Example 1 and parent strain W3110 were transformed with the prior IGF-I expression plasmid pYKM-I₁(Kim and Lee, *J. Biotechnol.*, 48, 97-105, 1996). The transformed strains were subjected to cell cultivation in the same manner as in Example 4. The expression of the IGF-I protein was induced by adding 1 mM IPTG at absorbance (O.D.) of 0.7 as measured with a spectrophotometer at a 600 nm wavelength. At 4 hours after induction of the human IGF-I protein, the culture solutions were collected by centrifugation, and then, each of the transformed culture solutions was fractionated into total protein in the same manner as in Example 4 (FIG. 13).

Figure 13:
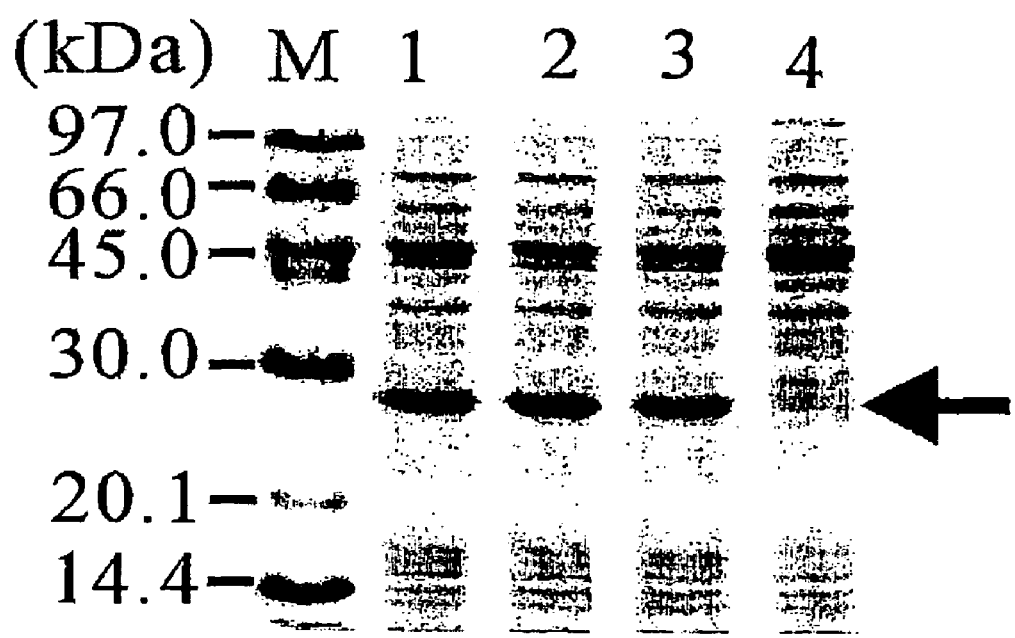
FIG. 13 is an electrophoretic picture showing the result of SDS-PAGE analysis of proteins obtained from recombinant *E. coli* W3110, WIbpA, WIbpB and WIB101 transformed with recombinant plasmid pYKM-I$_1$.

FIG. 13 is an electrophoretic picture showing the result of SDS-PAGE analysis of proteins obtained from recombinant E. coli WIbpA, WIbpB and WIB101 transformed with plasmid pYKM-I₁. In FIG. 13, lane M shows the molecular mass standard, lane 1 shows the result of fractionation into total protein of E. coli W3110 transformed with plasmid pYKM-I₁, lane 2 shows the result of fractionation into total protein of E. coli WIbpA transformed with plasmid pYKM-I₁, lane 3 shows the result of fractionation into total protein of E. coli WIbpB transformed with plasmid pYKM-I₁, and lane 4 shows the result of fractionation into total protein of E. coli W₁₀₁ transformed with plasmid pYKM-I₁. Also, the left arrow(←) represents the human IGF-I protein.

As shown in FIG. 13, in E. coli W3110, WIbpA and WIbpB, the human IGF-I protein was expressed at approximately the same amount, but in ibpA and ibpB genes-deleted E. coli WIB101, the target protein could not be produced in the cytoplasm. Thus, it could be found that ibpA or ibpB protein is required in the production of the target protein.

Furthermore, E. coli WIB101 constructed in Example 2 and parent stain W3110 were cotransformed with each of recombinant plasmids p184ΔCm, pACTacIbpA, pACTacIbpB, pACTacIbpAB, and pACIbpAB and with the prior IGF-I expression plasmid pYKM-I₁. The cell cultivation of E. coli and the induction of human IGF-I expression were conducted as described above.

Figure 14:
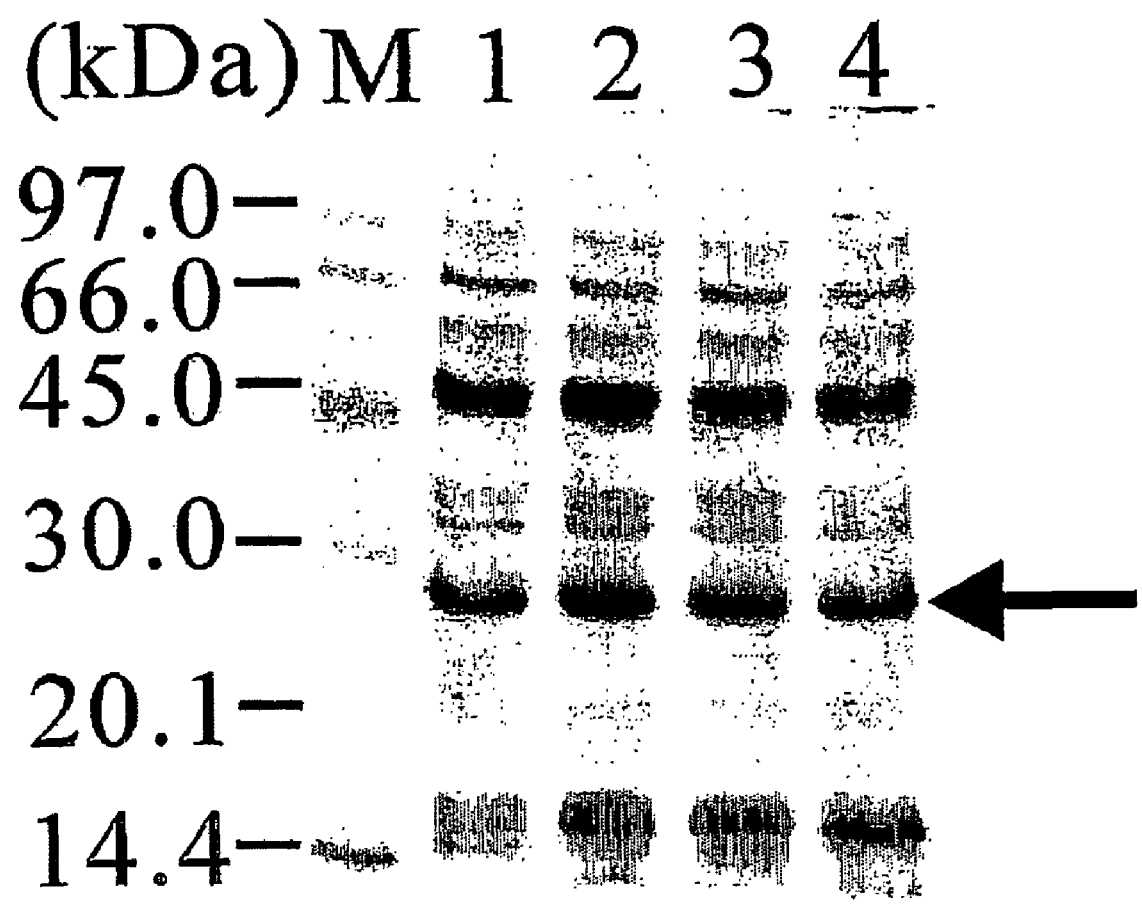
FIG. 14 is an electrophoretic picture showing the result of SDS-PAGE analysis of proteins obtained from recombinant *E. coli* W3110 cotransformed with each of recombinant plasmids p184ΔCm, pACTacIbpA, pACTacIbpB and pACTacIbpAB, and with recombinant plasmid pYKM-I$_1$.

FIG. 14 is an electrophoretic picture showing the result of SDS-PAGE analysis of proteins obtained from recombinant E. coli W3110 cotransformed with each of recombinant plasmids p184ΔCm, pACTacIbpA, pACTacIbpB and pACTacIbpAB and with plasmid pYKM-I₁. In FIG. 14, lane M shows the molecular mass standard, lane 1 represents the result of fractionation into total protein of E. coli W3110 cotransformed with recombinant plasmids p184ΔCm and pYKM-I₁, lane 2 shows the result of fractionation into total protein of E. coli W3110 cotransformed with recombinant plasmids pACTacIbpAB and pYKM-I₁, lane 3 shows the result of fractionation into total protein of E. coli W3110 cotransformed with recombinant plasmids pACTacIbpA and pYKM-I₁, and lane 4 shows the result of fractionation into total protein of E. coli W3110 cotransformed with recombinant plasmids pACTacIbpB and pYKM-I₁. Also, the left arrow(←) shows human IGF-I protein.

Figure 15:
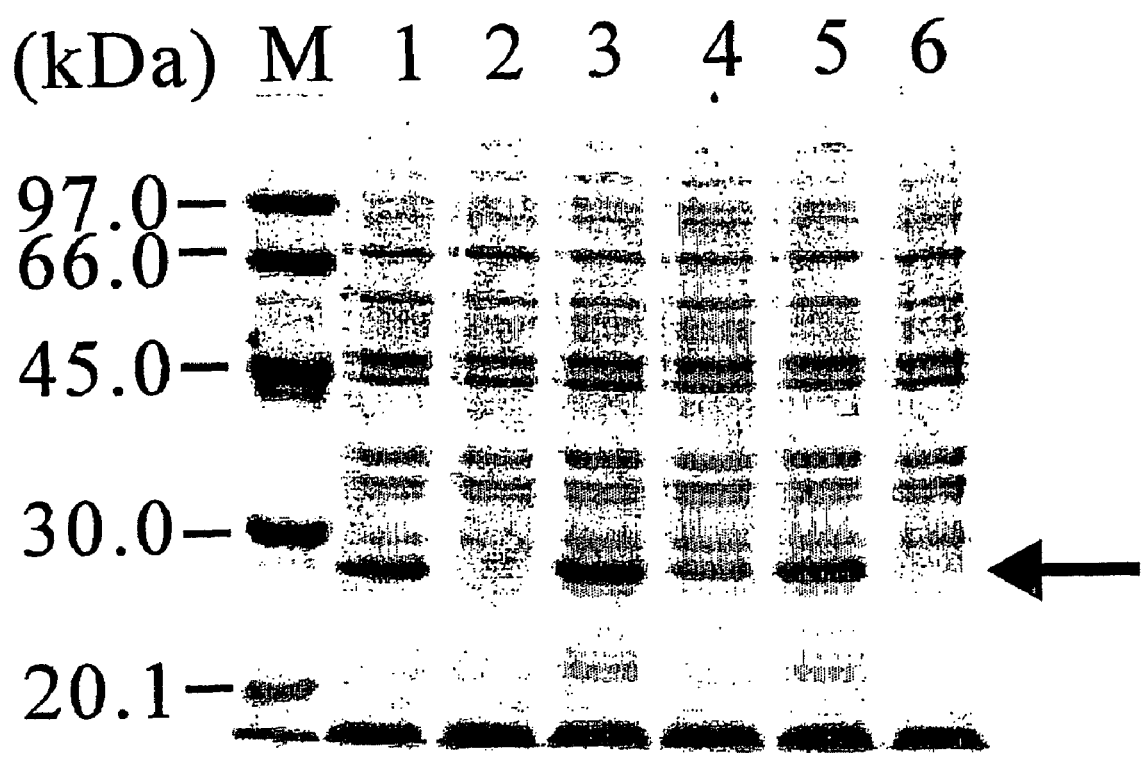
FIG. 15 is an electrophoretic picture showing the result of SDS-PAGE analysis of proteins obtained from recombinant *E. coli* W3110 and WIB101cotransformed with each of recombinant plasmids p184ΔCm, pACTacIbpAB and pACIbpAB, and with recombinant plasmid pYKM-I$_1$.

FIG. 15 is an electrophoretic picture showing the result of SDS-PAGE analysis of proteins obtained from recombinant E. coli W3110 and WIB101 cotransformed with each of recombinant plasmids p184ΔCm, pACTacIbpAB and pACIbpAB and with plasmid pYKM-I₁. In FIG. 15, lane M shows the molecular mass standard, lane 1 shows the result of fractionation into total protein of E. coli W3110 cotransformed with recombinant plasmids p184ΔCm and pYKM-I₁, lane 2 shows the result of fractionation into total protein of E. coli cotransformed with recombinant plasmids p184ΔCm and pYKM-I₁, lane 3 shows the result of fractionation into total protein of E. coli W3110 cotransformed with recombinant plasmids pACTacIbpAB and pYKM-I₁, lane 4 shows the result of fractionation into total protein of E. coli WIB101 cotransformed with recombinant plasmids pACTacIbpAB and pYKM-I₁, lane 5 shows the result of fractionation into total protein of E. coli W3110 cotransformed with recombinant plasmids pACIbpAB and pYKM-I₁, and lane 6 shows the result of fractionation into total protein of E. coli WIB101 cotransformed with recombinant plasmids pACIbpAB and pYKM-I₁. Also, the left arrow(←) shows human IGF-protein.

As shown in FIGS. 14 and 15, it was found that the coexpression of the ibpA, ibpB or ibpAB gene and the human IGF-I gene in E. coli W3110 resulted in about 2 times increase in production of human IGF-I protein as compared to the control group (E. coli W3110 cotransformed with p184ΔCm and pYKM-I₁). Also, it was found that the target protein could not be produced in the cytoplasm of ibpA and ibpB-deleted E. coli WIB101.

Accordingly, it could be found that the ibpA, ibpB or ibpAB gene enhanced the production of the target protein in the cytoplasm. In order to confirm if other target proteins, which are produced in the cytoplasm, can be applied in the present invention, additional tests were conducted with only ibpAB (pACTacIbpAB and pACIbpAB).

EXAMPLE 7

Production of IFN-γ (Interferon-γ) in the Cytoplasm Using ibpAB Expression System E. coli WIB101 constructed in Example 1 and parent strain W3110 were cotransformed with each of recombinant plasmids p184ΔCm, pACTacIbpA and pACIbpAB constructed in Example 2 and with plasmid p223-3IFN-γ of human interferon-γ protein constructed in Example 3. The transformed stains were subjected to cell cultivation in the same manner as in Example 4. The expression of the human interferon-γ protein was induced by adding 1 mM IPTG at absorbance (O.D.) of 0.7 as measured with a spectrophotometer at a 600 nm wavelength. At 4 hours after induction of the human interferon-γ protein, the culture solutions were collected by centrifugation, and then, were fractionated into total protein in the same manner as in Example 4 (FIG. 16).

Figure 16:
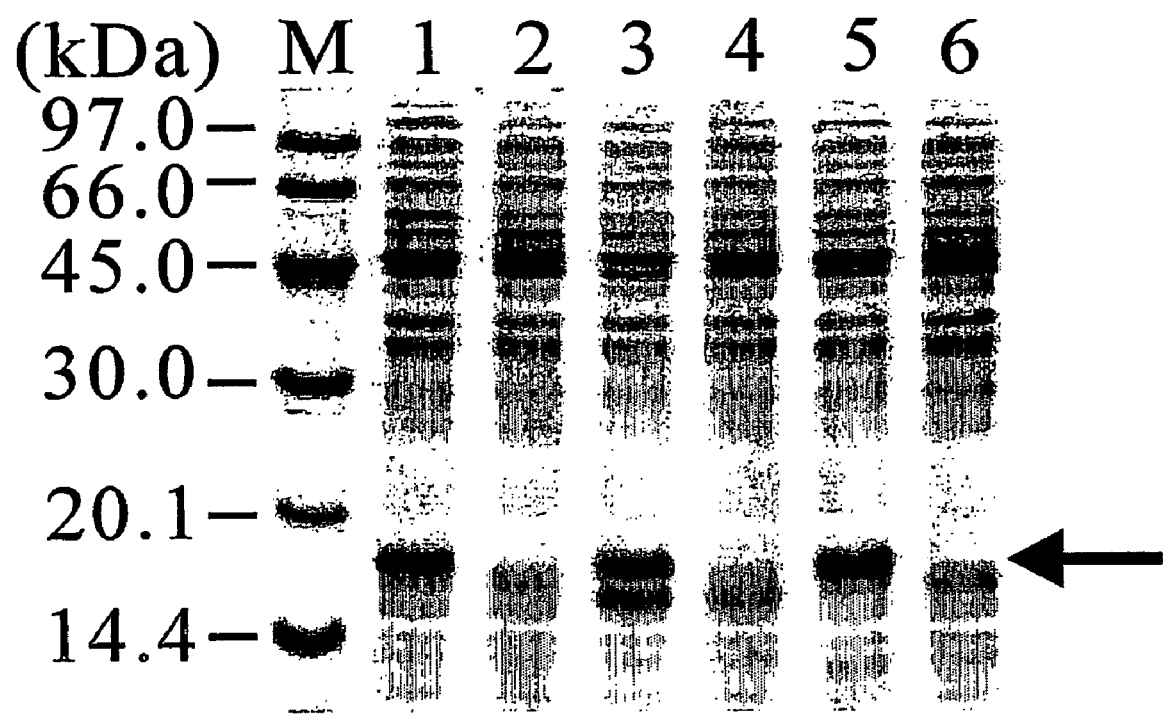
FIG. 16 is an electrophoretic picture showing the result of SDS-PAGE analysis of proteins obtained from recombinant *E. coli* W3110 and WIB101 cotransformed with each of recombinant plasmids p184ΔCm, pACTacIbpAB and pACIbpAB, and with recombinant plasmid p223-3IFN-γ.

FIG. 16 is an electrophoretic picture showing the result of SDS-PAGE analysis of proteins obtained from E. coli W3110 and WIB101 cotransformed with each of recombinant plasmids p184ΔCm, pACTacIbpA and pACIbpAB and with plasmid p223-3IFN-γ. In FIG. 16, lane M shows the molecular mass standard, lane 1 shows the result of fractionation into total protein of E. coli W3110 cotransformed with recombinant plasmids p184ΔCm and p223-3IFN-γ, lane 2 shows the result of fraction into total protein of E. coli WIB101 cotransformed with recombinant plasmids p184ΔCm and p223-3IFN-γ, lane 3 shows the result of fractionation into total protein of E. coli W3110 cotransformed with recombinant plasmids pACTacIbpAB and p223-3IFN-γ, lane 4 shows the result of fractionation into total protein of E. coli WIB101 cotransformed with recombinant plasmids pACTacIbpAB and p223-3IFN-γ, lane 5 shows the result of fractionation into total protein of E. coli W3110 cotransformed with recombinant plasmids pACIbpAB and p223-3IFN-γ, and lane 6 shows the result of fractionation into total protein of E. coli WIB101 cotransformed with recombinant plasmids pACIbpAB and p223-3IFN-γ. Also, the left arrow(←) shows human IFN-γ protein.

As shown in FIG. 16, it was found that the coexpression of the ibpAB gene and the IFN-γ gene in E. coli W3110 resulted in about 2 times increase in production of the human interferon-γ protein as compared to the control group (E. coli 3110 cotransformed with p184ΔCm and p223-3IFN-γ). Furthermore, it was found that the target protein could not be produced in the cytoplasm of ibpA and ibpB-deleted E. coli WIB101.

EXAMPLE 8

Production of Human Interleukin 12 β Chain Protein in the Cytoplasm Using ibpAB Expression System E. coli WIB101 constructed in Example 1 and parent strain W3110 were cotransformed with each of recombinant plasmids p184ΔCm, pACTacIbpA and pACIbpAB constructed in Example 2 and with plasmid pTac99IL-12p40 of human interleukin 12 β chain. The transformed strains were subjected to cell cultivation in the same manner as in Example 4. The expression of the human interleukin β chain protein was induced by adding 1 mM IPTG at absorbance (O.D.) of 0.7 as measured with a spectrophotometer at a 600 nm wavelength. At 4 hours after induction of the human interleukin β chain protein, the culture solutions were collected by centrifugation, and then, were fractionated into total protein in the same manner as in Example 4 (FIG. 17).

Figure 17:
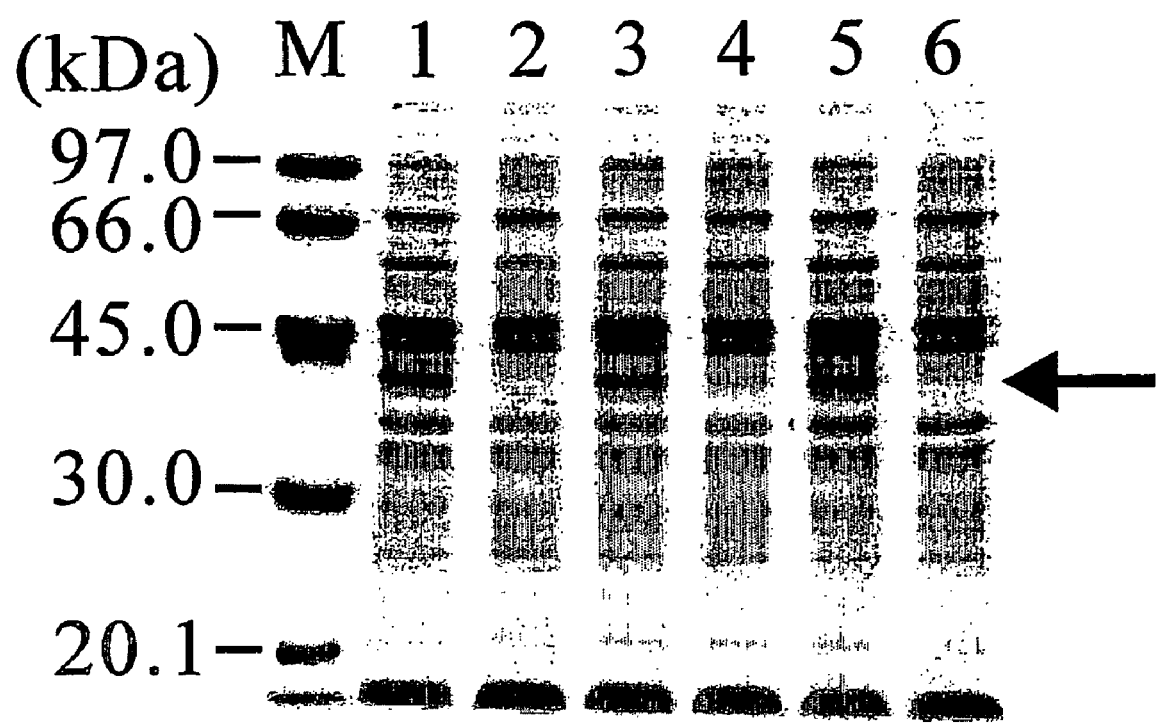
FIG. 17 is an electrophoretic picture showing the result of SDS-PAGE analysis of proteins obtained from recombinant *E. coli* W3110 and WIB101 cotransformed with each of recombinant plasmids p184ΔCm, pACTacIbpAB and pACIbpAB, and with recombinant plasmid pTac99IL-12p40.

FIG. 17 is an electrophoretic picture showing the result of SDS-PAGE gel electrophoresis of proteins obtained from recombinant E. coli W3110 and WIB101 cotransformed with each of recombinant plasmids p184ΔCm, pACTacIbpAB and pACIbpAB and with recombinant plasmid pTac99IL-12p40. In FIG. 17, lane M shows the molecular mass standard, lane 1 shows the result of fractionation into total protein of E. coli W3110 cotransformed with recombinant plasmids p184ΔCm and pTac99IL12p40, lane 2 shows the result of fractionation into total protein of E. coli WIB101 cotransformed with recombinant plasmids p184ΔCm and pTac99IL-12p40, lane 3 shows the result of fractionation into total protein of E. coli W3110 cotransformed with recombinant plasmids pACTacIbpAB and pTac99IL-12p40, lane 4 shows the result of fractionation into total protein of E. coli WIB101 cotransformed with recombinant plasmids pACTacIbpAB and pTac99IL-12p40, lane 5 shows the result of fractionation into total protein of E. coli W3110 cotransformed with recombinant plasmids pACIbpAB and pTac99IL-12p40, and lane 6 shows the result of fractionation into total protein of E. coli WIB101 cotransformed with recombinant plasmids pACIbpAB and pTac99IL-12p40. Also, the left arrow(←) shows human interleukin 12 β chain protein.

As shown in FIG. 17, it was found that the coexpression of ibpAB gene and interleukin 12 β chain gene in E. coli W3110 resulted in about 1.5 times increase in production of the human interleukin 12 β chain protein as compared to the control group (E. coli W3110 cotransformed with p184ΔCm and pTac99IL-12p40). Furthermore, it was found that the target protein could not be produced in the cytoplasm of ibpA and ibpB-deleted E. coli WIB101.

EXAMPLE 9

Production of A. victoria GFP (Green Fluorescent Protein) in the Cytoplasm Using ibpAB Expression System E. coli WIB101 in Example 1 and parent strain W3110 were cotransformed with each of recombinant plasmids p184ΔCm, pACTacIbpA and pACIbpAB constructed in Example 2 and with plasmid pTac99GFP of A. victoria green fluorescent protein (GFP) constructed in Example 3. The transformed strains were subjected to cell cultivation in the same manner as Example 4. The expression of GFP was induced by adding 1 mM IPTG at absorbance (O.D.) of 0.7 as measured with a spectrophotometer at a 600 nm wavelength. At 4 hours after induction of GFP, the culture solutions were collected by centrifugation, and then, fractionated into total protein, soluble protein and insoluble protein in the same manner as in Example 4 (FIGS. 18, 19 and 20).

Figure 18:
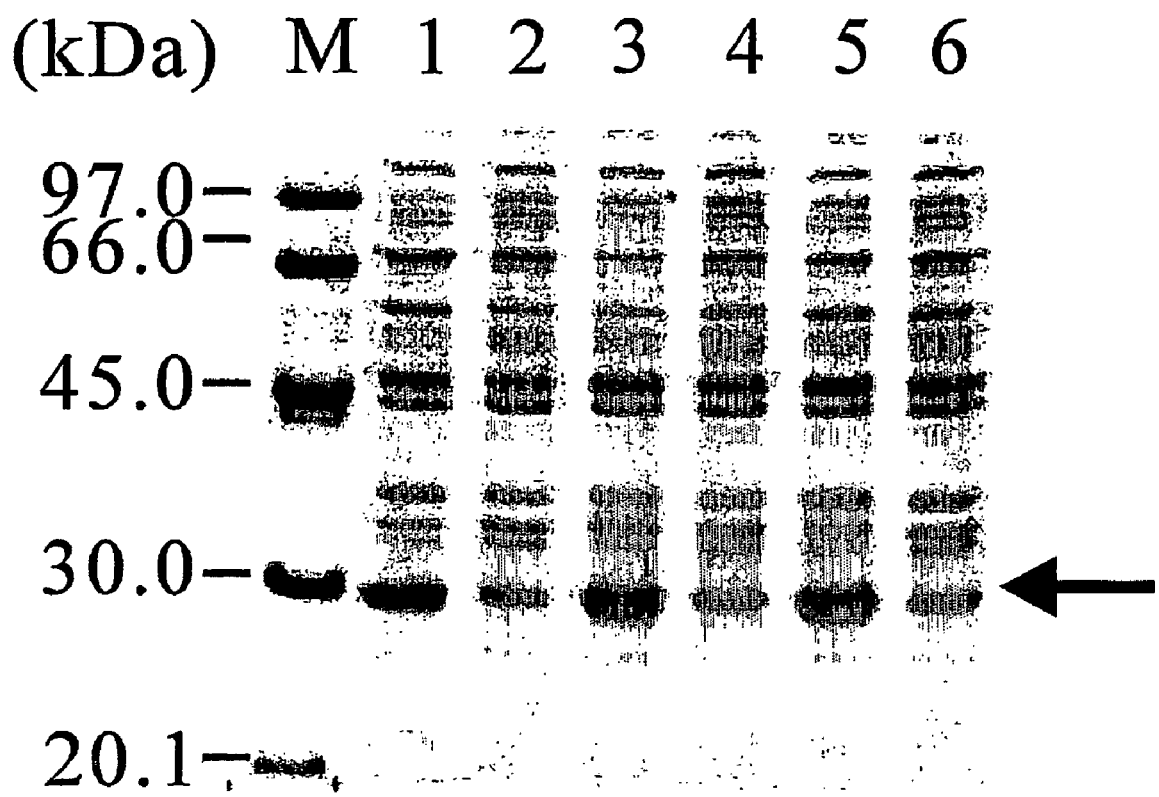
FIG. 18 is an electrophoretic picture showing the result of SDS-PAGE analysis of proteins obtained from recombinant *E. coli* W3110 and WIB101 cotransformed with each of recombinant plasmids p184ΔCm, pACTacIbpAB and pACIbpAB, and with recombinant plasmid pTac99GFP.

FIG. 18 is an electrophoretic picture showing the result of SDS-PAGE analysis of proteins obtained from E. coli W3110 and WIB101 cotransformed with each of recombinant plasmids p184ΔCm, pACTacIbpAB and pACIbpAB and with plasmid pTac99GFP. In FIG. 18, lane M shows the molecular mass standard, lane 1 shows the result of fractionation into total protein of E. coli W3110 cotransformed with recombinant plasmids p184ΔCm and pTac99GFP, lane 2 shows the result of fractionation into total protein of E. coli WIB101 cotransformed with recombinant plasmids p184ΔCm and pTac99GFP, lane 3 shows the result of fractionation into total protein of E. coli W3110 cotransformed with recombinant plasmids pACTacIbpAB and pTac99GFP, lane 4 shows the result of fractionation into total protein of E. coli WIB101 cotransformed with recombinant plasmids pACTacIbpAB and pTac99GFP, lane 5 shows the result of fractionation into total protein fractionation of E. coli W3110 cotransformed with recombinant plasmids pACIbpAB and pTac99GFP, and lane 6 shows the result of fractionation into total protein of E. coli WIB101 cotransformed with recombinant plasmids pACIbpAB and pTac99GFP. Also, the left arrow(←) shows GFP.

As shown in FIG. 18, it was found that the coexpression of the ibpAB gene and the GFP gene in E. coli W3110 resulted in about 2 times increase in production of GPF as compared to the control group (E. coli W3110 cotransformed with p184ΔCm and pTac99GFP). Also, it was found that the target protein could not be produced in the cytoplasm of ibpA and ibpB-deleted E. coli WIB101.

Figure 19:
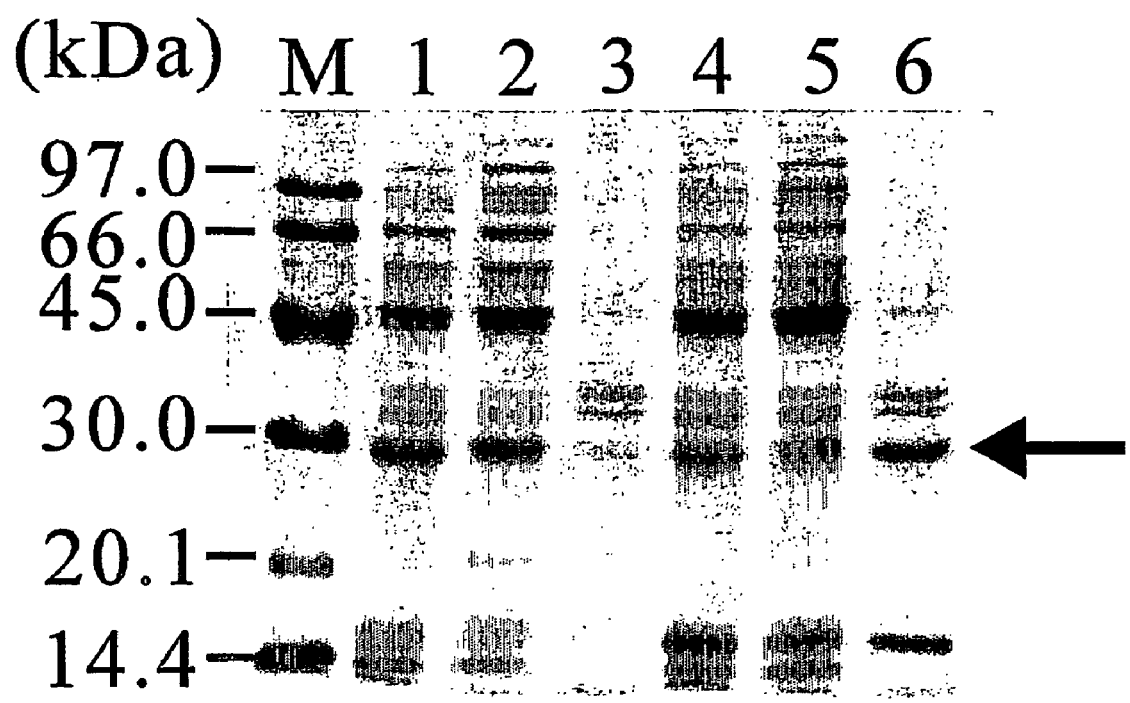
FIG. 19 is an electrophoretic picture showing the result of SDS-PAGE analysis of proteins obtained from recombinant *E. coli* W3110 cotransformed with each of recombinant plasmids p184ΔCm and pACTacIbpAB, and with recombinant plasmid pTac99GFP.
Figure 20:
FIG. 20 shows the green fluorescence of *Aequorea victoria* GFP.
Figure 20:
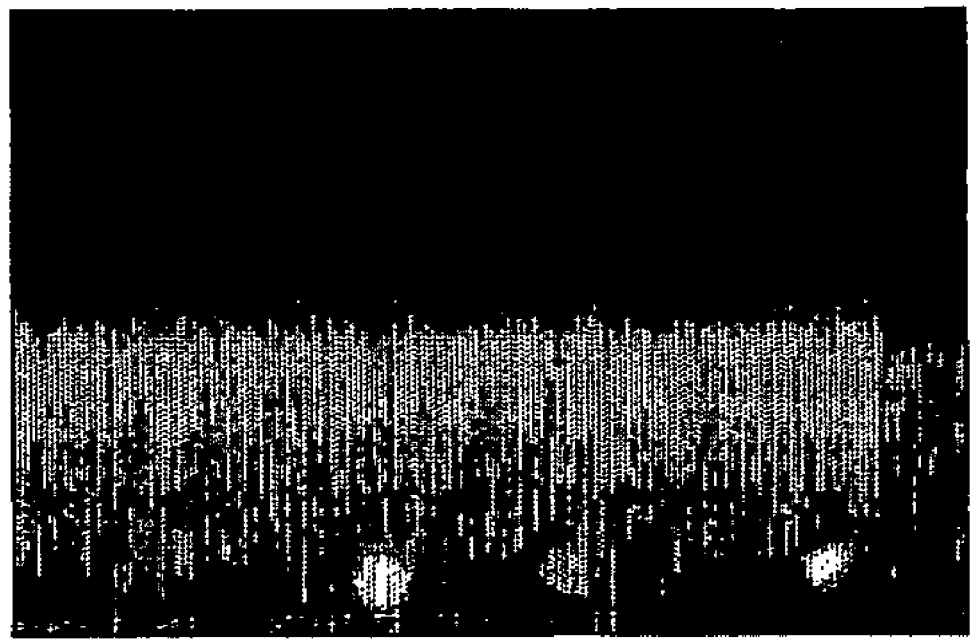
Figure 10:
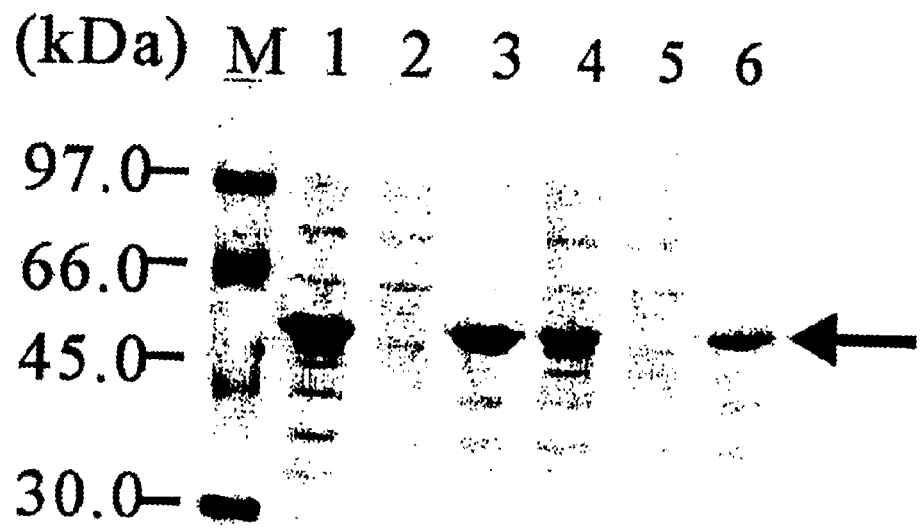
Figure 11:
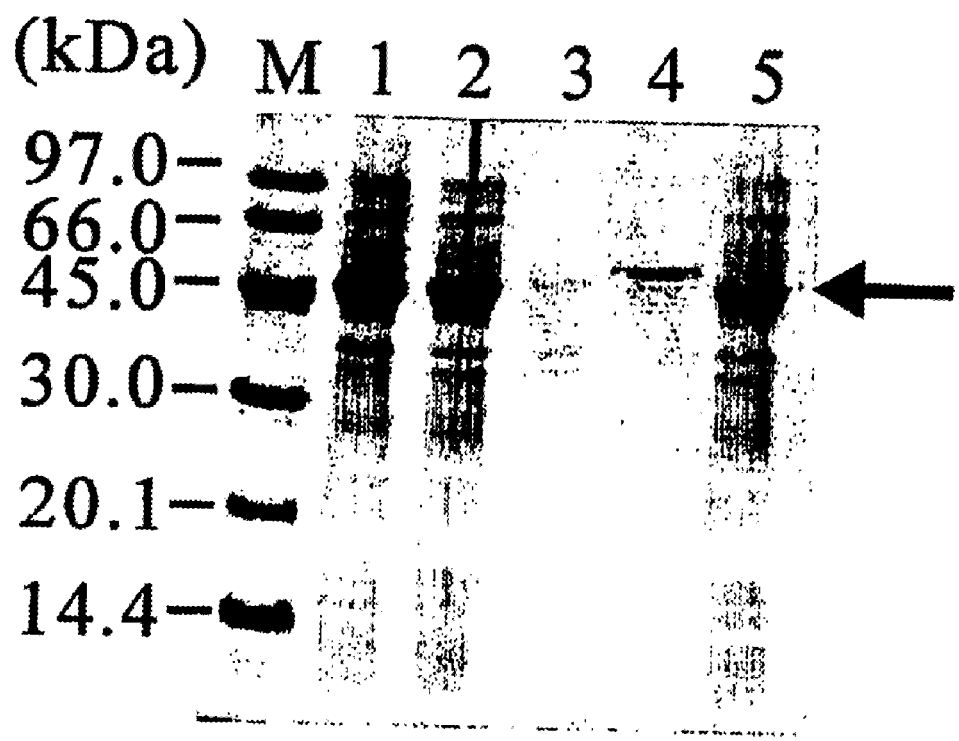

FIG. 19 is an electrophoretic picture showing the result of SDS-PAGE analysis of proteins obtained from E. coli W3110 cotransformed with each of p184ΔCm and pACTacIbpAB and with pTac99GFP. In FIG. 19, lane M shows the molecular mass standard, lanes 1-3 show the results of fractionation into total protein, soluble protein and insoluble protein of E. coli W3110 cotransformed with recombinant plasmids p184ΔCm and pTac99GFP, respectively, and lanes 4-6 show the results of fractionation into total protein, soluble protein and insoluble protein of E. coli W3110 cotransformed with recombinant plasmids pACTacIbpAB and pTac99GFP, respectively. Also, the left arrow(←) shows GFP.

As shown in FIG. 19, it was found that the coexpression of the IbpAB gene and GFP gene in E. coli W3110 allowed approximately 100% of the soluble target protein to be converted into an insoluble inclusion body.

FIG. 20 shows the green fluorescence of A. victoria GPF. In FIG. 20, lane 1 shows green fluorescence in E. coli W3110, lane 2 shows green fluorescence in E. coli W3110 (transformed with pTac99GFP), lane 3 shows green fluorescence in E. coli WIB101 (transformed with pTac99GFP), lane 4 shows green fluorescence in E. coli W3110 (cotransformed with pTac99GFP and pACTacIbpAB). This green fluorescence coincides with the result of the SDS-PAGE analysis conducted as described above. Thus, in the present invention, it was found that the formation of an inclusion body could be manipulated according to the characteristics and processing system of useful proteins as we desire.

INDUSTRIAL APPLICABILITY

As described above, the present invention provides two methods for producing target proteins using ibpA and/or ibpB genes coding for inclusion body-associated proteins of E. coli. The first method of the present invention is to increase the secretory production and activity of target proteins using ibpA and ibpB gene-deleted bacteria. The use of such bacteria allows target proteins to be secreted/produced in active and soluble form other than inactive and insoluble inclusion body form, and thus the improvement of productivity of a bioprocess be expected. The second method of the present invention is to improve the production of target proteins in the cytoplasm and also to produce the target proteins in insoluble inclusion body form, using ibpA and/or ibpB gene-amplified bacteria. By the introduction of this recombinant vector, the formation of the inclusion body can be manipulated as one desires, such that the inclusion body can be formed according to the characteristics and process system of useful proteins, and thus the improvement of productivity of a bioprocess can be expected.

What is claimed is:

1. An ibpA and ibpB genes-deleted bacterium which contains a gene coding for an exogenous protein, wherein the bacterium secretes the exogenous protein in an amount exceeding an amount of secretion by a wild-type bacterium.

2. The bacterium of claim 1, which additionally contains a signal sequence operably linked to the gene coding for said exogenous protein.

3. A method for the secretory production of an exogenous protein by microbial structure, which comprises culturing the bacterium of claim 1.

4. The method of claim 3, wherein the exogenous protein is leptin or alkaline phosphatase.

5. Plasmid pACTacIhpAB, pACIbpAB, pACTacIbpA or pACTacIbpB, which functions to amplify ibpA and/or ibpB genes in bacterium.

6. An ibpA and/or ibpB gene-amplified bacterium which contains a gene coding for an exogenous protein, wherein the exogenous protein in inclusion body form is produced in an amount exceeding an amount produced in a bacterium with an unamplitied ibpA or ibpB gene.

7. The bacterium of claim 6, wherein the ibpA and/or ibpB genes are amplified by a plasmid selected from the group consisting of plasmid pACTacIbpAB, pACIbpAB, pACTacIbpA and pACTacIbpB.

8. A method for producing an exogenous protein in inclusion body form by microbial culture, which comprises culturing an ibpA and/or ibpB gene-amplified bacterium.

9. The method of claim 8, wherein the exogenous protein is accumulated in the cytoplasm.

10. The method of claim 8, wherein the exogenous protein is produced in insoluble form.

11. The method of claim 8, wherein the exogenous protein is any one selected from the group consisting of IGF-I (insulin-like growth factor 1), INF-γ (interferon-γ), IL-12 β (interleukin 12 β chain), and GFP (green fluorescent protein).

12. A method for regulating the production form of an exogenous protein to soluble or insoluble form by amplifying or deleting ibpA and/or ibpB genes.

* * * * *

UNITED STATES PATENT AND TRADEMARK OFFICE
CERTIFICATE OF CORRECTION

PATENT NO. : 7,291,325 B2
APPLICATION NO. : 10/545849
DATED : November 6, 2007
INVENTOR(S) : Sang Yup Lee et al.

It is certified that error appears in the above-identified patent and that said Letters Patent is hereby corrected as shown below:

On The Title Page, "Primary Examiner—Rodney P Swartz" should be -- Primary Examiner—Rodney P. Swartz --.

Sheet 10 of the drawings (including FIG. 10) should be replaced with the enclosed Replacement Sheet 10 (including corrected FIG. 10).

Sheet 11 of the drawings (including FIG. 11) should be replaced with the enclosed Replacement Sheet 11 (including corrected FIG. 11).

Column 2, line 50: "Metlaznocoeus" should be -- Methanococcus --.

Column 3, line 4: "Ann. NZ Acad. Sci." should be -- Ann. N.Y. Acad. Sci. --.

Column 5, line 21: "WIB101cotransformed" should be -- WIB101 cotransformed --.

Column 11, line 47: "higher tan" should be -- higher than --.

Column 12, line 50: "Factor)" should be -- Factor-I) --.

Column 23, line 62 (claim 6): "unamplitied" should be -- unamplified --.

Column 24, line 55 (claim 11): "Factor I" should be -- Factor-I --.

Signed and Sealed this

Eighth Day of April, 2008

JON W. DUDAS
*Director of the United States Patent and Trademark Office*

SEQUENCE LISTING

<160> NUMBER OF SEQ ID NOS: 22

<210> SEQ ID NO 1
<211> LENGTH: 40
<212> TYPE: DNA
<213> ORGANISM: Artificial Sequence
<220> FEATURE:
<223> OTHER INFORMATION: Synthetic Construct

<400> SEQUENCE: 1
ataagaatgc ggccgccagc tgtggatcac cgaaactgat            40

<210> SEQ ID NO 2
<211> LENGTH: 30
<212> TYPE: DNA
<213> ORGANISM: Artificial Sequence
<220> FEATURE:
<223> OTHER INFORMATION: Synthetic Construct

<400> SEQUENCE: 2
gctctagatg catagactga gggggcagca            30

<210> SEQ ID NO 3
<211> LENGTH: 31
<212> TYPE: DNA
<213> ORGANISM: Artificial Sequence
<220> FEATURE:
<223> OTHER INFORMATION: Synthetic Construct

<400> SEQUENCE: 3
ggaattcttt cgactgttta agatatttcg g            31

<210> SEQ ID NO 4
<211> LENGTH: 34
<212> TYPE: DNA
<213> ORGANISM: Artificial Sequence
<220> FEATURE:
<223> OTHER INFORMATION: Synthetic Construct

<400> SEQUENCE: 4
acgcgtcgac ggagaaaatc cccagcacta ccgg            34

<210> SEQ ID NO 5
<211> LENGTH: 26
<212> TYPE: DNA
<213> ORGANISM: Artificial Sequence
<220> FEATURE:
<223> OTHER INFORMATION: Synthetic Construct

<400> SEQUENCE: 5
gctctagagc cacgttgtgt ctcaaa            26

<210> SEQ ID NO 6
<211> LENGTH: 27
<212> TYPE: DNA
<213> ORGANISM: Artificial Sequence
<220> FEATURE:
<223> OTHER INFORMATION: Synthetic Construct

<400> SEQUENCE: 6
cgaattctta gaaaaactca tcgagca                                           27

<210> SEQ ID NO 7
<211> LENGTH: 83
<212> TYPE: DNA
<213> ORGANISM: Artificial Sequence
<220> FEATURE:
<223> OTHER INFORMATION: Synthetic Construct

<400> SEQUENCE: 7
atgcgtaact ttgatttatc cccgctttac cgttctgcta ttggatttga ccgtttgttt      60
gccacgttgt gtctcaaaat ctc                                              83

<210> SEQ ID NO 8
<211> LENGTH: 80
<212> TYPE: DNA
<213> ORGANISM: Artificial Sequence
<220> FEATURE:
<223> OTHER INFORMATION: Synthetic Construct

<400> SEQUENCE: 8
ttagttgatt tcgatacggc gcggtttttt cgcttccgga atcacgcgtt cgagatcgat      60
ttagaaaaac tcatcgagca                                                  80

<210> SEQ ID NO 9
<211> LENGTH: 83
<212> TYPE: DNA
<213> ORGANISM: Artificial Sequence
<220> FEATURE:
<223> OTHER INFORMATION: Synthetic Construct

<400> SEQUENCE: 9
atgcgtaact tcgatttatc cccactgatg cgtcaatgga tcggttttga caaactggcc      60
gccacgttgt gtctcaaaat ctc                                              83

<210> SEQ ID NO 10
<211> LENGTH: 80
<212> TYPE: DNA
<213> ORGANISM: Artificial Sequence
<220> FEATURE:
<223> OTHER INFORMATION: Synthetic Construct

<400> SEQUENCE: 10
ttagctattt aacgcgggac gttcgctgat agcgatacgc tgcgctgcga tgggttcagg      60
ttagaaaaac tcatcgagca                                                  80

<210> SEQ ID NO 11
<211> LENGTH: 29
<212> TYPE: DNA
<213> ORGANISM: Artificial Sequence
<220> FEATURE:
<223> OTHER INFORMATION: Synthetic Construct

<400> SEQUENCE: 11
ggaattcatg cgtaactttg atttatccc                                        29

<210> SEQ ID NO 12
<211> LENGTH: 31
<212> TYPE: DNA
<213> ORGANISM: Artificial Sequence
<220> FEATURE:
<223> OTHER INFORMATION: Synthetic Construct

<400> SEQUENCE: 12
cccaagcttt tagttgattt cgatacggcg c                    31

<210> SEQ ID NO 13
<211> LENGTH: 34
<212> TYPE: DNA
<213> ORGANISM: Artificial Sequence
<220> FEATURE:
<223> OTHER INFORMATION: Synthetic Construct

<400> SEQUENCE: 13
ggaattcatg cgtaacttcg atttatcccc actg                 34

<210> SEQ ID NO 14
<211> LENGTH: 36
<212> TYPE: DNA
<213> ORGANISM: Artificial Sequence
<220> FEATURE:
<223> OTHER INFORMATION: Synthetic Construct

<400> SEQUENCE: 14
cccaagcttt tagctattta acgcgggacg ttcgct               36

<210> SEQ ID NO 15
<211> LENGTH: 29
<212> TYPE: DNA
<213> ORGANISM: Artificial Sequence
<220> FEATURE:
<223> OTHER INFORMATION: Synthetic Construct

<400> SEQUENCE: 15
ggaattcatg cgtaactttg atttatccc                       29

<210> SEQ ID NO 16
<211> LENGTH: 36
<212> TYPE: DNA
<213> ORGANISM: Artificial Sequence
<220> FEATURE:
<223> OTHER INFORMATION: Synthetic Construct

<400> SEQUENCE: 16
cccaagcttt tagctattta acgcgggacg ttcgct               36

<210> SEQ ID NO 17
<211> LENGTH: 29
<212> TYPE: DNA
<213> ORGANISM: Artificial Sequence
<220> FEATURE:
<223> OTHER INFORMATION: Synthetic Construct

<400> SEQUENCE: 17
ggaattccag ctgtggatca ccgaaactg                       29

<210> SEQ ID NO 18
<211> LENGTH: 28
<212> TYPE: DNA
<213> ORGANISM: Artificial Sequence
<220> FEATURE:
<223> OTHER INFORMATION: Synthetic Construct

<400> SEQUENCE: 18
ggaattcaga acgtgccgaa atatctta                        28

<210> SEQ ID NO 19

-continued

```
<211> LENGTH: 29
<212> TYPE: DNA
<213> ORGANISM: Artificial Sequence
<220> FEATURE:
<223> OTHER INFORMATION: Synthetic Construct

<400> SEQUENCE: 19
ggaattcatg agtaaaggag aagaacttt                                       29

<210> SEQ ID NO 20
<211> LENGTH: 28
<212> TYPE: DNA
<213> ORGANISM: Artificial Sequence
<220> FEATURE:
<223> OTHER INFORMATION: Synthetic Construct

<400> SEQUENCE: 20
cccaagcttt tatttgatga gctcatcc                                        28

<210> SEQ ID NO 21
<211> LENGTH: 31
<212> TYPE: DNA
<213> ORGANISM: Artificial Sequence
<220> FEATURE:
<223> OTHER INFORMATION: Synthetic Construct

<400> SEQUENCE: 21
ggaattcatg tgttactgcc aggacccata t                                    31

<210> SEQ ID NO 22
<211> LENGTH: 30
<212> TYPE: DNA
<213> ORGANISM: Artificial Sequence
<220> FEATURE:
<223> OTHER INFORMATION: Synthetic Construct

<400> SEQUENCE: 22
cccaagcttt tactgggatg ctcttcgacc                                      30
```